(12) United States Patent
Udo

(10) Patent No.: US 8,606,368 B2
(45) Date of Patent: Dec. 10, 2013

(54) ELECTRODE UNIT, ELECTRODE SYSTEM, ELECTRODE IMPLANTING APPARATUS, AND ELECTRODE IMPLANTING SYSTEM

(75) Inventor: Yoshiro Udo, Tokyo (JP)

(73) Assignee: Olympus Corporation, Tokyo (JP)

( * ) Notice: Subject to any disclaimer, the term of this patent is extended or adjusted under 35 U.S.C. 154(b) by 111 days.

(21) Appl. No.: 13/013,179

(22) Filed: Jan. 25, 2011

(65) Prior Publication Data

US 2011/0184437 A1 Jul. 28, 2011

(30) Foreign Application Priority Data

Jan. 26, 2010 (JP) ................................ P2010-014215
Mar. 19, 2010 (JP) ................................ P2010-064647

(51) Int. Cl.
*A61N 1/04* (2006.01)

(52) U.S. Cl.
USPC .......................................... 607/118; 607/116

(58) Field of Classification Search
USPC ................................................ 607/118, 116
See application file for complete search history.

(56) References Cited

U.S. PATENT DOCUMENTS

| 4,920,979 | A | 5/1990 | Bullara |
| 5,095,905 | A | 3/1992 | Klepinski |
| 6,093,197 | A * | 7/2000 | Bakula et al. ................. 606/129 |
| 2008/0172116 | A1 * | 7/2008 | Mrva et al. .................... 607/115 |
| 2010/0241207 | A1 * | 9/2010 | Bluger .......................... 607/118 |

FOREIGN PATENT DOCUMENTS

| JP | 2005-058456 | 3/2005 |
| JP | 2005-211683 | 8/2005 |
| JP | 2008-067978 | 3/2008 |

* cited by examiner

*Primary Examiner* — Christopher D Koharski
*Assistant Examiner* — Michael Carey
(74) *Attorney, Agent, or Firm* — Scully, Scott, Murphy & Presser, P.C.

(57) ABSTRACT

An electrode system which includes: an electrode unit capable of switching at least a part of its shape between a curved shape and a stretched shape, wherein in the curved shape the electrode unit is wound around a predetermined linear tissue, and wherein in the stretched shape the electrode unit is flat; and a treatment tool that switches the shape of the at least a part of the electrode unit between the curved shape and the stretched shape, wherein the electrode unit includes: an insulating member formed in a sheet shape out of an elastic material; and an electrode that is disposed on a first surface which is an inside surface of a curvature when the insulating member has a curved shape and which applies a predetermined voltage.

22 Claims, 39 Drawing Sheets

US 8,606,368 B2

ELECTRODE UNIT, ELECTRODE SYSTEM, ELECTRODE IMPLANTING APPARATUS, AND ELECTRODE IMPLANTING SYSTEM

BACKGROUND OF THE INVENTION

1. Field of the Invention

The present invention relates to an electrode unit and an electrode system that apply an electrical stimulus to a linear tissue, and an electrode implanting apparatus and an electrode implanting system that implant an electrode unit in a state where it is wound around a linear tissue.

Priority is claimed on Japanese Patent Application No. 2010-014215, filed Jan. 26, 2010, and Japanese Patent Application No. 2010-064647, filed Mar. 19, 2010, the contents of which are incorporated herein by reference.

2. Description of Related Art

Conventionally, an electrode unit having an electrode was wound around an elongated linear tissue to apply a predetermined voltage thereto or to measure current flowing in the linear tissue. In the medical field, stimulus generators applying an electrical stimulus directly or indirectly to a body tissue (linear tissue) such as a nerve tissue or a muscle for treatment has been conventionally known such as a nerve stimulator, a pain reliever, an epilepsy treatment apparatus, and a muscle stimulator. The stimulus generators have a power source therein and are used in a state where they are buried in a body along with an electrode lead transmitting the electrical stimulus.

In general, the electrode lead includes at least one electrode unit giving an electrical stimulus to a body tissue or detecting electrical excitement generated in the body tissue, an electrical connector for electrical connection to a stimulus generator, and a lead body disposed between the electrode unit and the stimulus generator so as to transmit an electrical stimulus.

For example, a nerve-stimulating electrode assembly (electrode unit) described in U.S. Pat. No. 4,920,979 includes a pair of electrodes formed in a helical shape so as to extend in the opposite directions and the pair of electrodes are applied to the nerve tissue so as to be wound therearound. In an electrode system (electrode unit) described in U.S. Pat. No. 5,095,905, a backbone-like member extending in a predetermined direction and finger-like members alternately extending in a rib-like shape from the backbone-like member are integrally formed out of a polymer material having biocompatibility. An electrode is disposed in the inner surface of the finger-like member and the electrode comes in contact with a nerve tissue when the finger-like member of the electrode system is wound around the nerve tissue.

A treatment tool described in Japanese Patent Application, First Publication No. 2005-211683 includes a curved portion (adjusting mechanism) curved in a predetermined direction. In the treatment tool, it is possible to freely adjust the direction of a distal end by changing the curved state of the curved portion.

SUMMARY OF THE INVENTION

According to an aspect of the invention, there is provided an electrode system including: an electrode unit capable of switching at least a part of its shape between a curved shape and a stretched shape, wherein in the curved shape the electrode unit is wound around a predetermined linear tissue, and wherein in the stretched shape the electrode unit is flat; and a treatment tool that switches the shape of the at least a part of the electrode unit between the curved shape and the stretched shape. Here, the electrode unit includes: an insulating member faulted in a sheet shape out of an elastic material; and an electrode that is disposed on a first surface which is an inside surface of a curvature when the insulating member has a curved shape and which applies a predetermined voltage.

In the electrode system, the electrode unit may have the curved shape in a natural state where an external force does not act thereon, and the treatment tool may include a stretch mechanism that switches the curved shape of the electrode unit to the stretched shape, holds the stretched shape, and releases the holding.

In the electrode system, the insulating member may include an electrode-side engagement portion extending in parallel to the curving direction of the insulating member. Here, the stretch mechanism may include: a stretch member that is formed to extend in a predetermined direction out of a material having higher rigidity than that of the insulating member and detachably engages with the electrode-side engagement portion of the insulating member; and a contact member that comes in contact with the insulating member when the stretch member is disengaged from the insulating member.

In the electrode system, the electrode-side engagement portion may be formed at both ends in an axis line direction of the curvature when the insulating member has a curved shape. In this case, the stretch mechanism may further include: two stretch members; and a member gap adjusting section that supports the two stretch members to be arranged in a direction intersecting the predetermined direction in which each of the two stretch members extend and that adjusts the gap between the two stretch members in the intersecting direction.

In the electrode system, the stretch mechanism may pinch the electrode unit from the first surface of the insulating member and a second surface opposite to the first surface so as to hold the electrode unit in the stretched shape, and may release the pinching.

In the electrode system, the stretch mechanism may include: a tubular member that receives the electrode unit extending in a predetermined electrode-unit stretching direction by stretching the curvature of the electrode unit having the curved shape so as to allow the electrode-unit stretching direction to be parallel to the axis line direction of the tubular member; and an extrusion member that extrudes the electrode unit in the tubular member to the distal end of the tubular member in the axis line direction.

In the electrode system, in a state where the curvature of the electrode unit having the curved shape is stretched to extend in a predetermined electrode-unit stretching direction, the stretch mechanism may include: a first pinch member that is disposed on the first surface of the insulating member and is movable to a first side in the electrode-unit stretching direction; a second pinch member that is disposed on the second surface of the insulating member; and a support member that comes in contact with the first side of the insulating member in the electrode-unit stretching direction.

In the electrode system, the stretch mechanism may include: a first end holding portion that holds a first end in the curving direction of the insulating member in the at least a part of the insulating member; a second end engaging portion that engages with a second end in the curving direction of the insulating member in the at least a part of the insulating member; and a gap adjusting mechanism that adjusts the gap between the first end holding portion and the second end engaging portion.

In the electrode system, the electrode unit may have the stretched shape in a natural state where an external force does not act thereon. In this case, the treatment tool may include a curving mechanism that switches the shape of the electrode unit from the stretched shape to the curved shape.

In the electrode system, the insulating member may include an electrode-side engagement portion extending in parallel to the first surface, and the electrode unit may include a curving member that is formed in a curved shape so as to be wound around a predetermined linear tissue out of an elastic material having higher rigidity than that of the insulating member and that engages with the electrode-side engagement portion. Here, the curving mechanism may include: a grasp portion that grasps the insulating member; a reinforcing member that is formed to extend in a predetermined direction with constant rigidity and that detachably engages with the electrode-side engagement portion of the insulating member; and an extrusion portion that holds the curving member in a state where the curving member is stretched in the curved-portion stretching direction in which the curvature of the curving member is stretched and that extrudes the curving member, which has been stretched in the curved-portion stretching direction, in the curved-portion stretching direction.

According to another aspect of the invention, there is provided an electrode unit which has a curved shape in which at least a part of its shape is curved to be wound around a predetermined linear tissue in a natural state when an external force does not act thereon and which can switch the curved shape to a stretched shape in which the at least a part of its shape is flat, which includes: an insulating member that is formed in a sheet shape out of an elastic material; and an electrode that is disposed on an inside surface of a curvature formed by a curved shape of the insulating member and which applies a predetermined voltage. Here, the insulating member includes an electrode-side engagement portion that extends in parallel to a curving direction in which the insulating member is curved.

According to another aspect of the invention, there is provided an electrode unit which has a stretched shape in which at least a part of its shape is stretched in a natural state when an external force does not act thereon and which can switch the stretched shape to a curved shape in which the at least a part of its shape is curved to be wound around a predetermined linear tissue, which includes: an insulating member that is formed in a sheet shape out of an elastic material; an electrode that is disposed on a first surface of the insulating member which is an inside surface of a curvature when the insulating member has a curved shape and which applies a predetermined voltage; and a curving member that is formed in a curved shape out of an elastic material having higher rigidity than that of the insulating member. Here, the insulating member includes an electrode-side engagement portion that extends in parallel to the first surface of the insulating member and that engages with the curving member.

According to still another aspect of the invention, there is provided an electrode implanting apparatus which includes: the above-mentioned electrode system, in which the treatment tool includes a long insertion section and the stretch mechanism, is disposed at a distal end of the insertion section; an adjusting mechanism that adjusts the orientation of the electrode unit held by the stretch mechanism; and an operation unit that is disposed in a proximal end of the insertion section and that operates the stretch mechanism and the adjusting mechanism.

In the electrode implanting apparatus, the insulating member may include an electrode-side engagement portion that extends in parallel to a curving direction in which the insulating member is curved, and the stretch mechanism may include: a stretch member of which a distal end detachably engages with the electrode-side engagement portion of the insulating member and a proximal end is connected to the operation unit; and a holder that is connected to the distal end of the insertion section and that comes in contact with the electrode unit.

In the electrode implanting apparatus, the adjusting mechanism may curve the distal end of the insertion section in a direction which is separated from an axis line of the insertion section.

In the electrode implanting apparatus, the insertion section may include: a long insertion section body; and a rotating member that is connected to the distal end of the insertion section body so as to rotate about a predetermined axis line and of which a distal end is connected to the holder. In this case, the adjusting mechanism may include an operation member of which a distal end is connected to the rotating member and a proximal end is connected to the operation unit.

In the electrode implanting apparatus, the treatment tool may include a fixing mechanism that locks and unlocks the position of the proximal end of the operation member to and from the insertion section.

In the electrode implanting apparatus, the stretch member may be disposed so as to be located outside the curvature of the operation member when the distal end of the insertion section is curved.

In the electrode implanting apparatus, the adjusting mechanism may curve the distal end of the insertion section in a first direction and a second direction which depart from the axis line of the insertion section and intersect each other.

In the electrode implanting apparatus, the stretch mechanism may rotate about the axis line of the stretch member.

According to still another aspect of the invention, there is provided an electrode implanting system which includes: the above-mentioned electrode implanting apparatus; and an observation device that includes a long observation insertion section.

DETAILED DESCRIPTION OF THE INVENTION

First Embodiment

Hereinafter, an electrode system according to a first embodiment of the invention will be described with reference to FIGS. 1 to 20. In the following embodiment, it is assumed that the electrode system is used along with a nerve stimulator.

Figure 1:
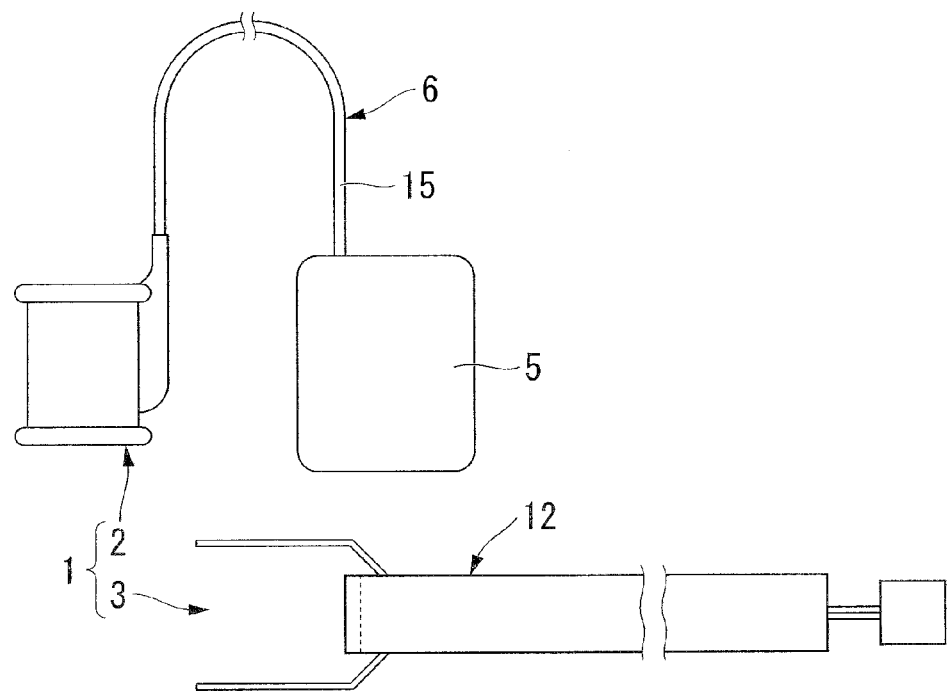
FIG. 1 is a plan view illustrating an electrode system according to a first embodiment of the invention.

As shown in FIG. 1, an electrode system 1 according to the first embodiment includes an electrode unit 2 applying a predetermined voltage to a nerve tissue (linear tissue) and a treatment tool 3 used to attach the electrode unit 2 to the nerve tissue. In this embodiment, the electrode system 1 is used along with a nerve stimulator 5 generating an electrical stimulus to be given to a nerve tissue and a lead body 6 electrically connecting the electrode unit 2 to the nerve stimulator 5.

Figure 2:
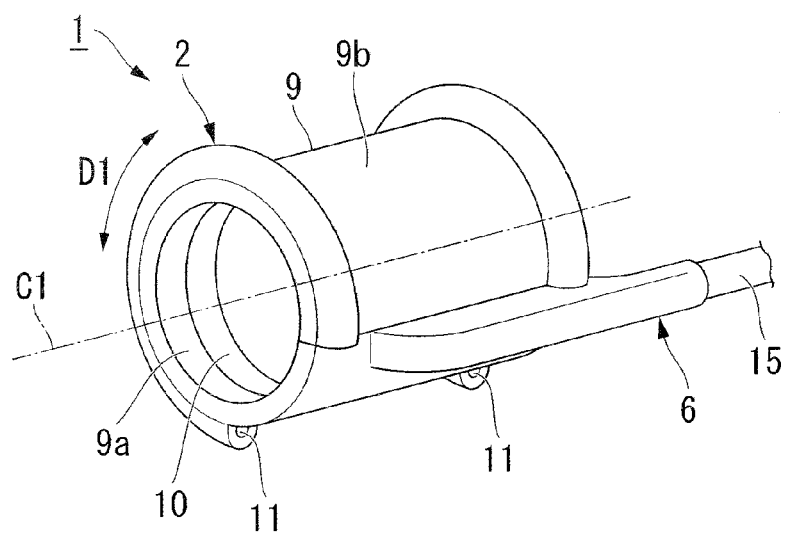
FIG. 2 is a perspective view illustrating an electrode unit of the electrode system according to the first embodiment in a natural state when an external force does not act thereon.
Figure 3:
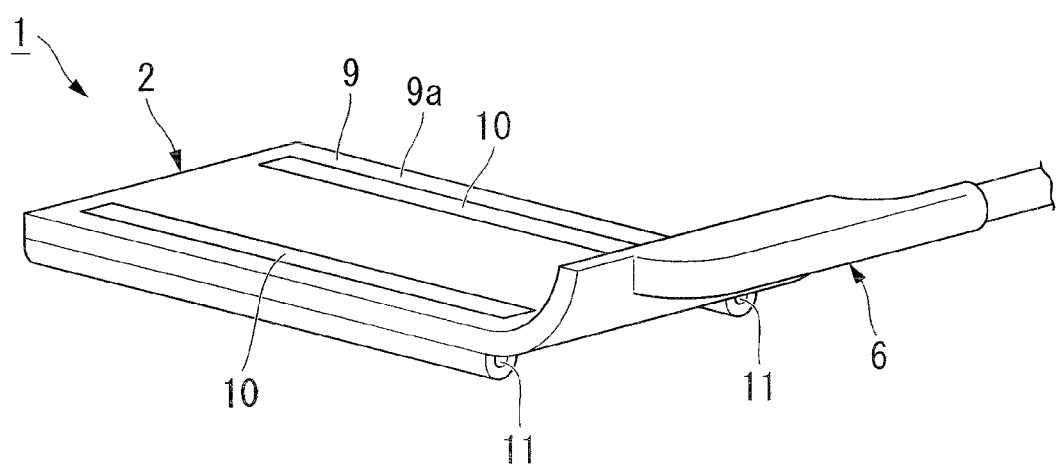
FIG. 3 is a perspective view illustrating the electrode unit in a state where the curvature of the electrode unit is stretched into a stretched shape.

As shown in FIGS. 2 and 3, the electrode unit 2 can switch (change) its entire shape from one to the other of a curved shape in which the electrode unit is curved to be wound around a nerve tissue and a stretched shape in which the electrode unit is flat. In this embodiment, the electrode unit 2 has the curved shape shown in FIG. 2 in a natural state where an external force does not act thereon, and can switch the shape into the stretched shape shown in FIG. 3.

The electrode unit 2 includes an electrode support (insulating member) 9 formed in a sheet shape out of an elastic material and a pair of electrodes 10 formed in a first surface 9a which is the inside surface of the curvature when the electrode support 9 is in the curved shape.

The electrode support 9 is formed of a soft insulating material such as silicone so as not to damage a nerve tissue.

The electrodes 10 are disposed on both ends in an axis line direction C1 of the curvature in the curved shape of the electrode support 9 and are exposed from the first surface 9a of the electrode support 9 so as to extend in parallel to a curving direction D1 in which the electrode support 9 is curved. The electrodes 10 are formed of metal or the like having elasticity and high biocompatibility and have the curved shape in the natural state. That is, in this embodiment, the electrodes 2 have the curved shape in the natural state due to the elastic force of the electrodes 10 and can be changed to a stretched shape.

Figure 4:
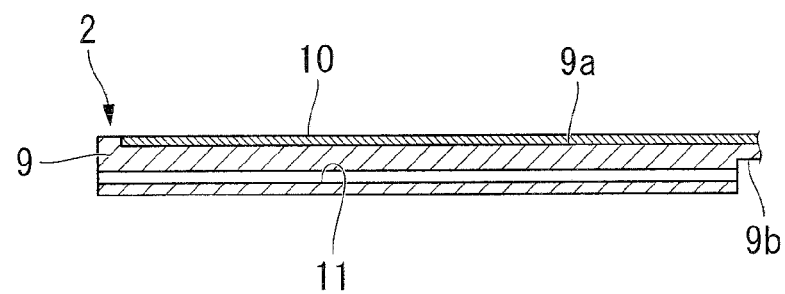
FIG. 4 is a partial sectional view illustrating a state where the electrode unit has a stretched shape.

As shown in FIGS. 2 and 4, guide holes (electrode-side engagement portions) 11 which are a through-hole having a circular cross-section are formed at both ends in the axis line direction C1 of a second surface 9b opposite to the first surface 9a of the electrode support 9. In this embodiment, the guide holes 11 are formed to extend in parallel to the curving direction D1 in portions protruding outwardly from the second surface 9b.

Stretch members 13 stretching the electrode unit 2 in the stretched shape engage with the guide holes 11 as described later, but it is preferable that the guide holes 11 and the electrodes 10 are matched with each other in position in the axis line direction C1. This is because the electrode unit 2 can be effectively stretched in the stretched shape against the elastic force of the electrodes 10 by the use of the stretch members 13.

As shown in FIG. 1, the treatment tool 3 serves to switch the shape of the electrode unit 2 from one to the other of the curved shape and the stretched shape. In this embodiment, the treatment tool 3 includes a stretch mechanism 12 switching the curved shape of the electrode unit 2 to the stretched shape, holding the stretched shape, and releasing the holding.

Figure 5:
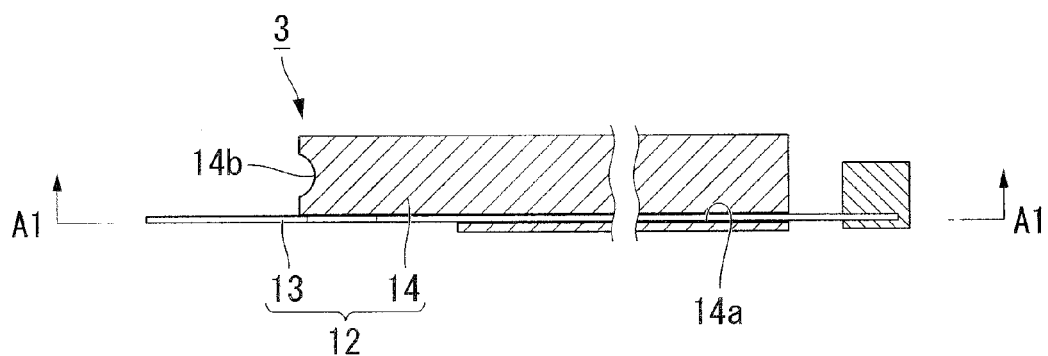
FIG. 5 is a side sectional view illustrating a treatment tool of the electrode system.
Figure 6:
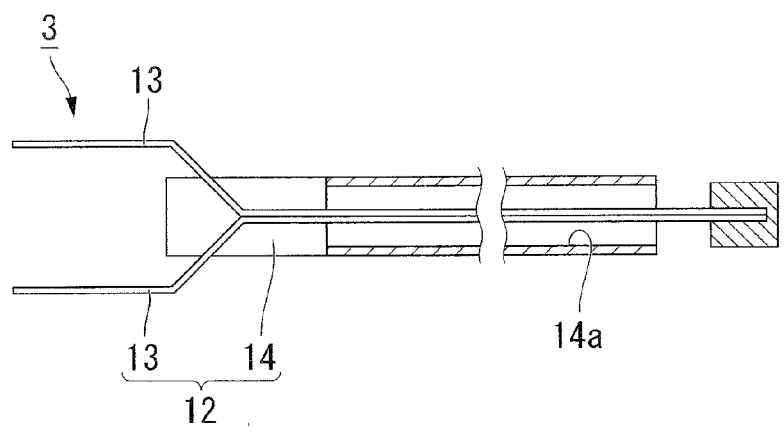
FIG. 6 is a sectional view taken along line A1-A1 of FIG. 5.

As shown in FIGS. 5 and 6, the stretch mechanism 12 includes a pair of stretch members 13 formed to extend in a predetermined direction out of a material having higher rigidity than that of the electrode support 9 and a pressing rod (contact member) 14 coming in contact with the electrode unit 2 at the time of separating the stretch members 13 from the guide holes 11 of the electrode support 9.

The stretch members 13 are formed of metal or the like and distal ends thereof can detachably engage with the guide holes 11 of the electrode support 9. The pair of stretch members 13 are fixed to each other on proximal end side thereof to form a substantially Y shape as a whole. The proximal end of the stretch members 13 is inserted through a support hole 14a extending in the length direction of the pressing rod 14 at a proximal end of the pressing rod 14. In this way, the stretch member 13 can slide relative to the pressing rod 14.

A concave portion 14b corresponding to a distal shape of the lead body 6 brought into contact with the pressing rod 14 is formed at the distal end of the pressing rod 14.

The nerve stimulator 5 includes a power source not shown, detects an electrical signal generated from a nerve tissue, and generates an electrical stimulus with a predetermined waveform. Accordingly, the nerve stimulator 5 can detect a signal of a nerve tissue acquired with the electrode unit 2 and apply an electrical stimulus to the nerve tissue as needed.

The lead body 6 has a known configuration and includes a coil (not shown) electrically connecting the electrodes 10 and the nerve stimulator 5 and a flexible insulating tube 15 (see FIG. 1) covering the outer circumference of the coil.

Figure 7:
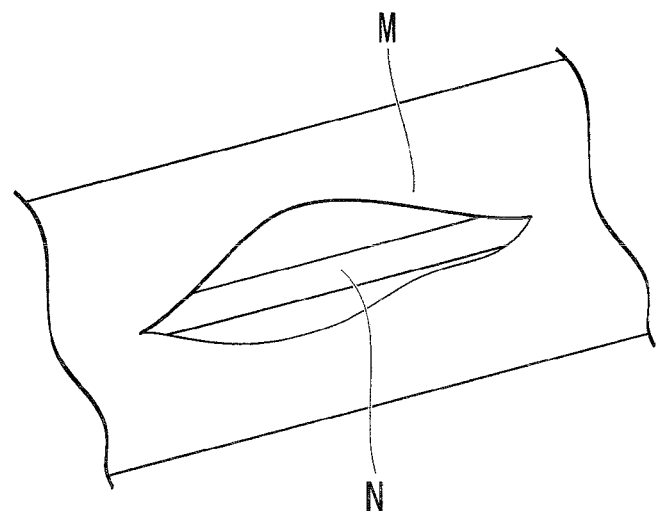
FIG. 7 is a diagram illustrating a state of a patient's nerve tissue.

A process of attaching the electrode unit 2 to a nerve tissue N shown in FIG. 7 using the electrode system 1 having the above-mentioned configuration will be described below.

First, an operator attaches a trocar T (see FIG. 9) not shown to a patient's chest region and observes the inside of the chest cavity by the use of a thoracoscope not shown. Then, the operator inserts a cutting treatment tool such as a knife not shown into the chest cavity and cuts a peripheral tissue M such as a membrane located around a desired nerve tissue N to expose the nerve tissue N.

Figure 8:
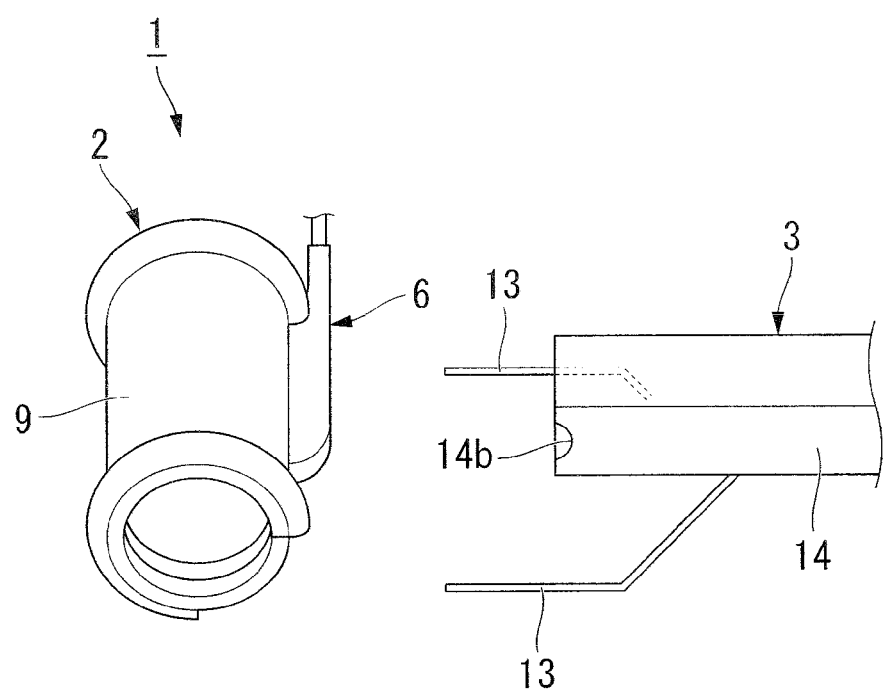
FIG. 8 is a diagram illustrating a process of inserting a stretch member of the treatment tool through the electrode unit.
Figure 9:
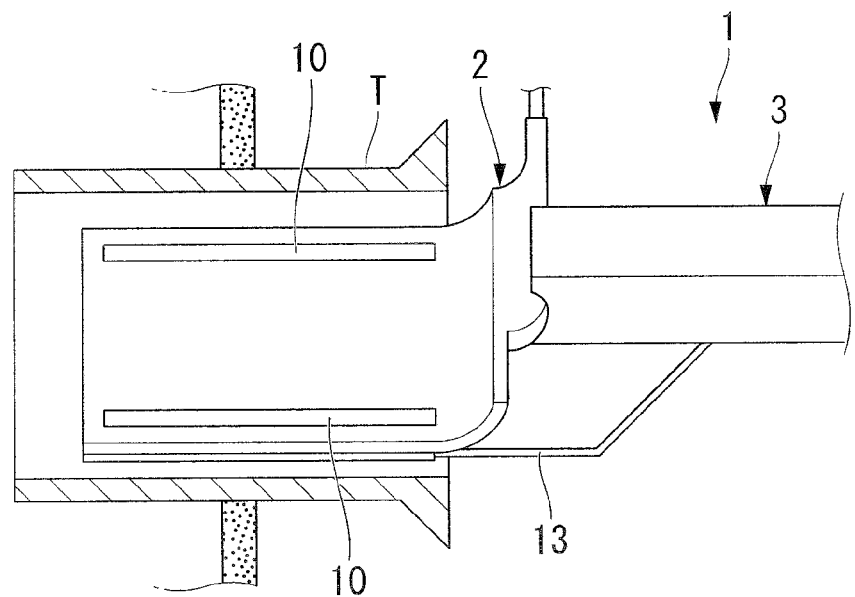
FIG. 9 is a diagram illustrating a process of inserting the electrode unit and the treatment tool through a trocar.

As shown in FIG. 8, the operator engages the concave portion 14b of the pressing rod 14 with a distal end of the lead body 6, whereby the pressing rod 14 comes in contact with the electrode unit 2 with the lead body 6 interposed therebetween. The operator inserts and engages the distal ends of the stretch members 13 into and with the guide holes of the electrode unit 2 having the curved shape, whereby the electrode unit 2 is switched to the stretched shape (stretching step) as shown in FIG. 9. Then, the operator inserts the electrode unit 2 and the treatment tool 3, which are coupled to each other in a body, through the trocar T.

Figure 10:
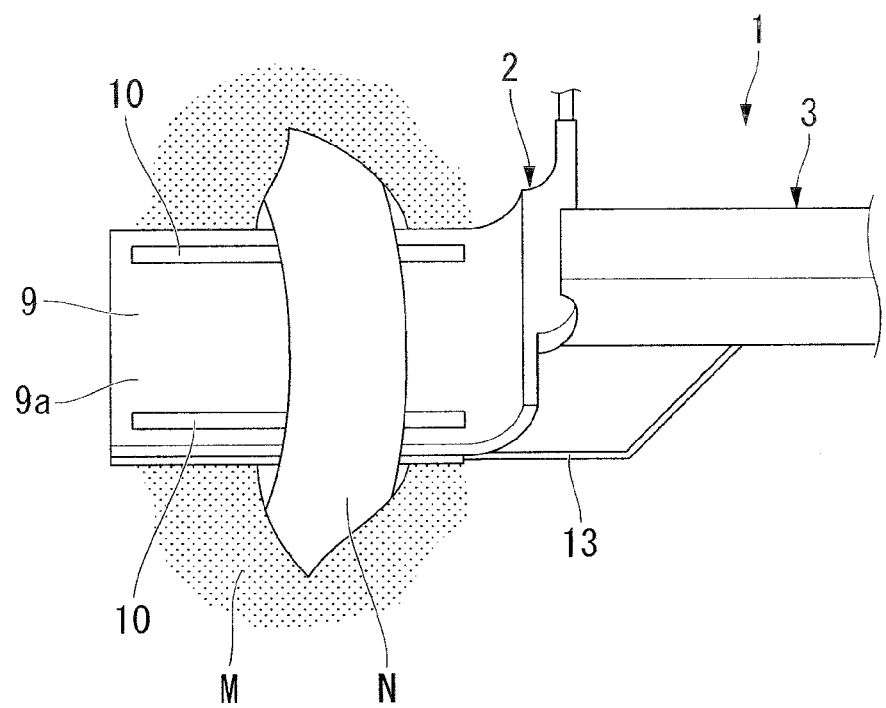
FIG. 10 is a diagram illustrating a state where the electrode unit having a stretched shape is inserted between a nerve tissue and a membrane.

As shown in FIG. 10, the distal end of the electrode unit 2 switched to the stretched shape so as to oppose the first surface 9a of the electrode unit 2 to the nerve tissue N is inserted between the nerve tissue N and the peripheral tissue M (positioning step).

Figure 11:
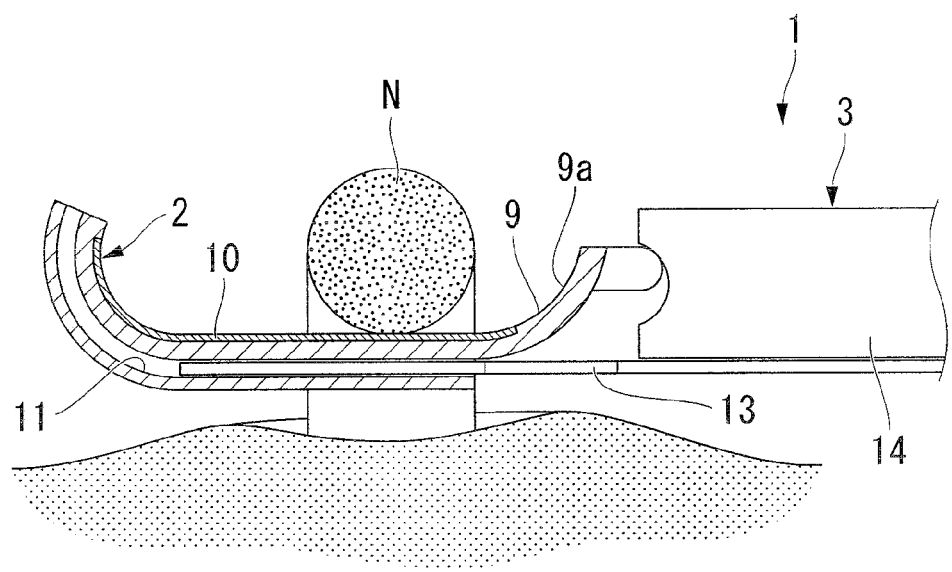
FIG. 11 is a diagram illustrating a process of separating a stretch member from the electrode unit.
Figure 12:
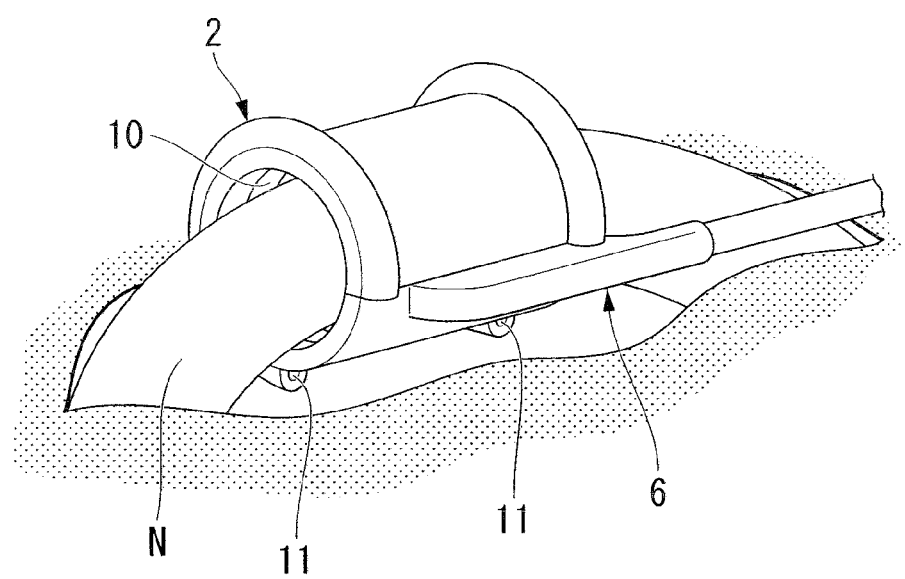
FIG. 12 is a diagram illustrating a state where the electrode unit is attached to a nerve tissue.
Figure 13:
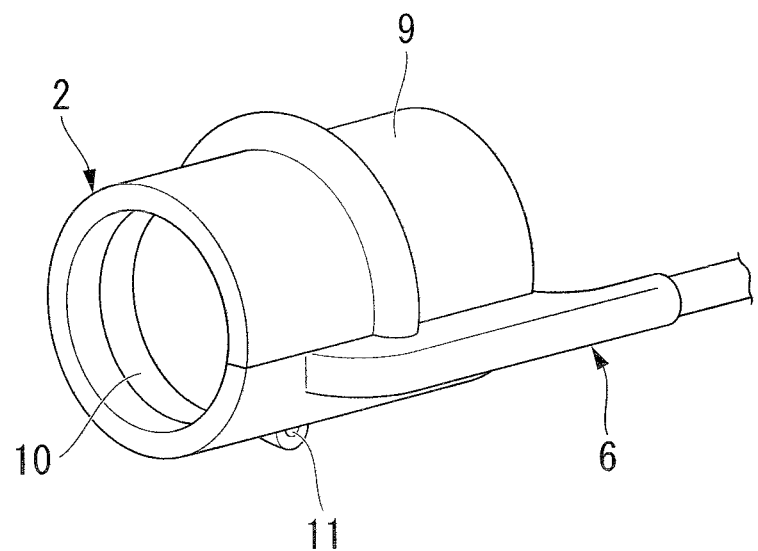
FIG. 13 is a perspective view illustrating an electrode unit of an electrode system according to a modified example of the first embodiment of the invention.
Figure 14:
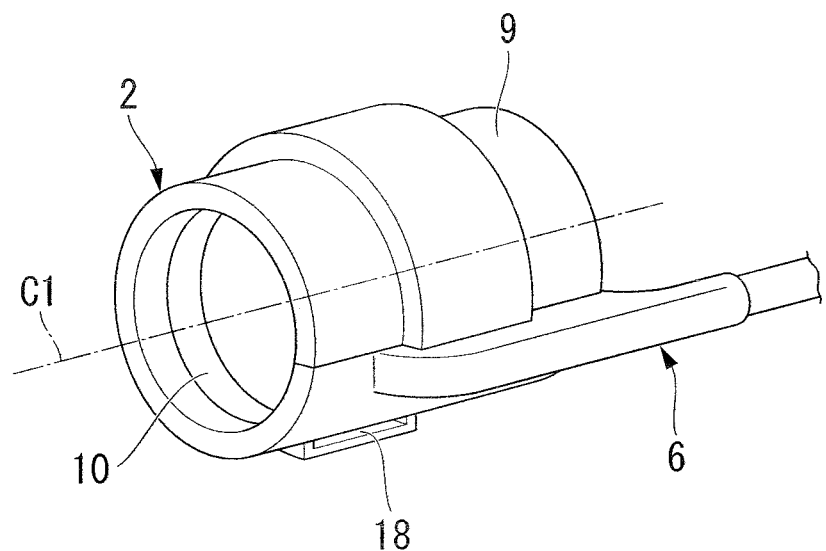
FIG. 14 is a perspective view illustrating an electrode unit of an electrode system according to another modified example of the first embodiment of the invention.

As shown in FIG. 11, by pulling out the stretch members 13 from the guide holes 11 in a state where the position of the pressing rod 14 is fixed, the electrode unit 2 is restored to the curved shape as shown in FIG. 12, whereby the electrode unit 2 is wound around the nerve tissue N and the electrodes 10 come in contact with the nerve tissue N.

The electrodes 10 do not necessarily come in contact with the nerve tissue N all over the circumference of the nerve tissue N, but the electrodes 10 can come in contact with only a part of the entire circumference of the nerve tissue N. When the range in which the electrodes 10 come in contact with the nerve tissue N is great, it is possible to effectively transmit an electrical stimulus generated from the nerve stimulator 5 to the nerve tissue N. When the contact range is small, it is possible to suppress the damage on the nerve tissue N resulting from the winding of the electrodes 10 on the nerve tissue N. Accordingly, the degree of contact may be properly set by an operator or a doctor.

Subsequently, the operator buries the lead body 6 and the nerve stimulator 5 under the patient's skin and ends the process.

As described above, in the electrode system 1 according to this embodiment, the operator switches the electrode unit 2 to the stretched shape by the use of the treatment tool 3 and locates the electrode unit 2 so as to oppose one surface 9 thereof to the nerve tissue N. By switching the electrode unit 2 to the curved shape by the use of the treatment tool 3, the operator winds the electrode unit 2 on the nerve tissue N while bringing the electrodes 10 into contact with the nerve tissue N.

Accordingly, for example, even when the nerve tissue N is located among complex tissues, it is possible to satisfactorily and easily attach the electrode unit 2 to a patient's nerve tissue N to apply a predetermined voltage thereto by getting the electrode unit 2 closer to the nerve tissue N after switching the electrode unit to the stretched shape.

By inserting and engaging the stretch members 13 through and with the guide holes 11 of the electrode unit 2 having a curved shape, the electrode unit 2 is switched to the stretched shape. Then, by pulling out the stretch members 13 from the guide holes 11 while bringing the pressing rod 14 into contact with the electrode unit 2 in a state where the first surface 9a of the electrode unit 2 goes close to the nerve tissue N, the electrode unit 2 is returned to the curved shape, thereby easily winding the electrode unit 2 on the nerve tissue N.

Since the electrodes 10 are disposed on only the first surface 9a of the electrode support 9, it is possible to prevent the electrodes 10 from coming in contact with tissues other than the nerve tissue N.

In this embodiment, the guide holes 11 are formed at both ends in the axis line direction C1 of the electrode support 9. However, the number of guide holes 11 formed in the electrode support 9 is not particularly limited, and may be three or more or may be one as in a modified example shown in FIG. 13.

In this embodiment, the cross-sectional shape of the guide holes 11 formed in the electrode support 9 is circular. However, the cross-sectional shape of the guide holes 11 is not limited to the circular shape, but may be an elliptical shape or a polygonal shape such as a rectangular shape like a guide hole (electrode-side engagement portion) 18 shown in FIG. 14. By setting the cross-sectional shape of the guide holes to a polygonal shape and setting the cross-sectional shape of the stretch members to a shape corresponding to the cross-sectional shape of the guide holes, it is possible to prevent the stretch members from rotating around their axis line in the guide holes, thereby stably changing the shape.

Figure 15:
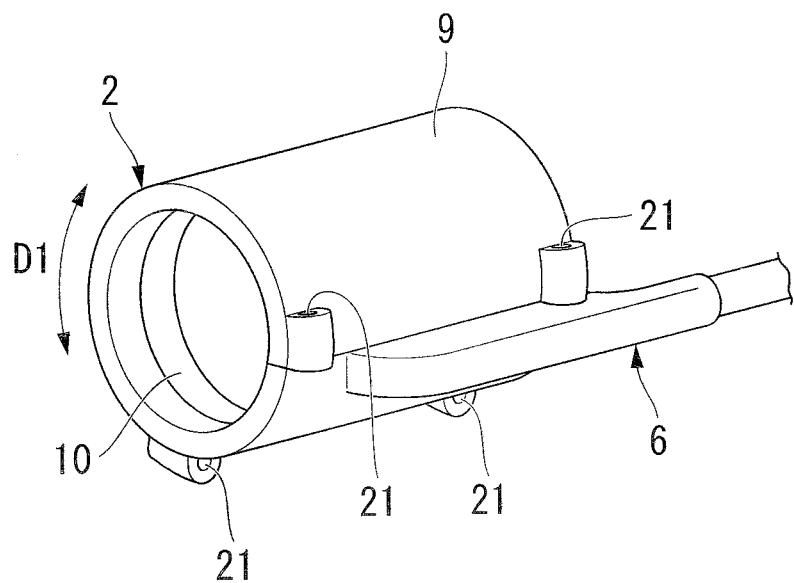
FIG. 15 is a perspective view illustrating an electrode unit of an electrode system according to another modified example of the first embodiment of the invention.

In this embodiment, the guide holes 11 are formed to extend in parallel to the curving direction D1, but a plurality of guide holes may be formed at an interval in the curving direction D1 like guide holes 21 shown in FIG. 15.

Figure 16:
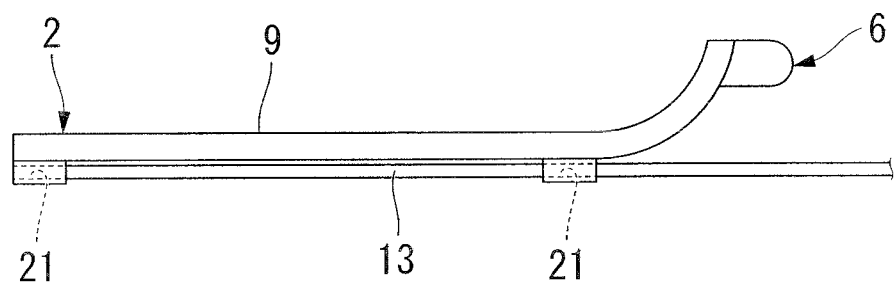
FIG. 16 is a side view illustrating a state where the stretch member of the treatment tool is inserted through the electrode unit of the electrode system.
Figure 17:
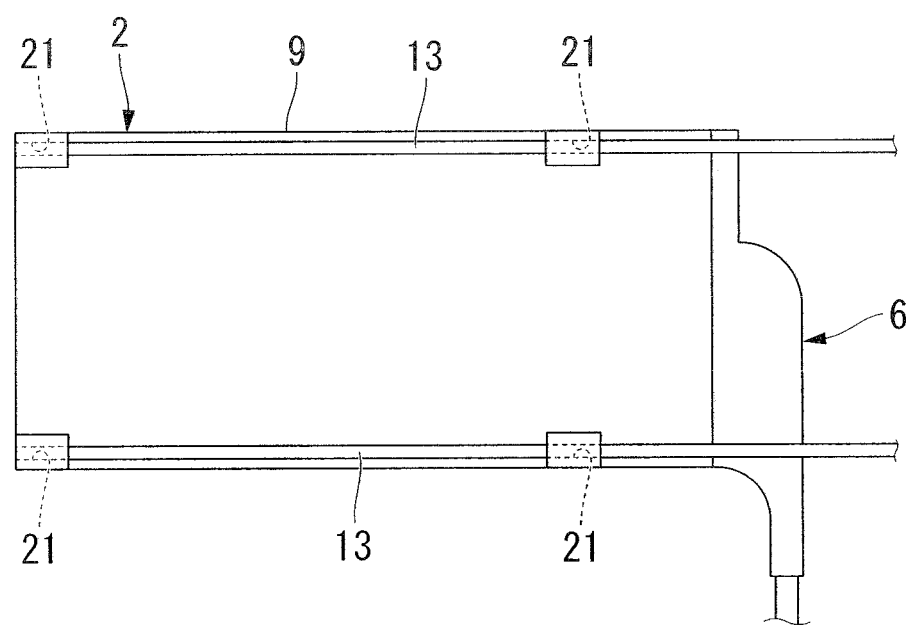
FIG. 17 is a bottom view illustrating a state where the stretch member of the treatment tool is inserted through the electrode unit.

In this case, when the electrode unit 2 is stretched in the stretched shape and the stretch members 13 are engaged with the guide holes 21, each stretch member 13 is engaged with the plurality of guide holes 21 as shown in FIGS. 16 and 17.

Figure 18:
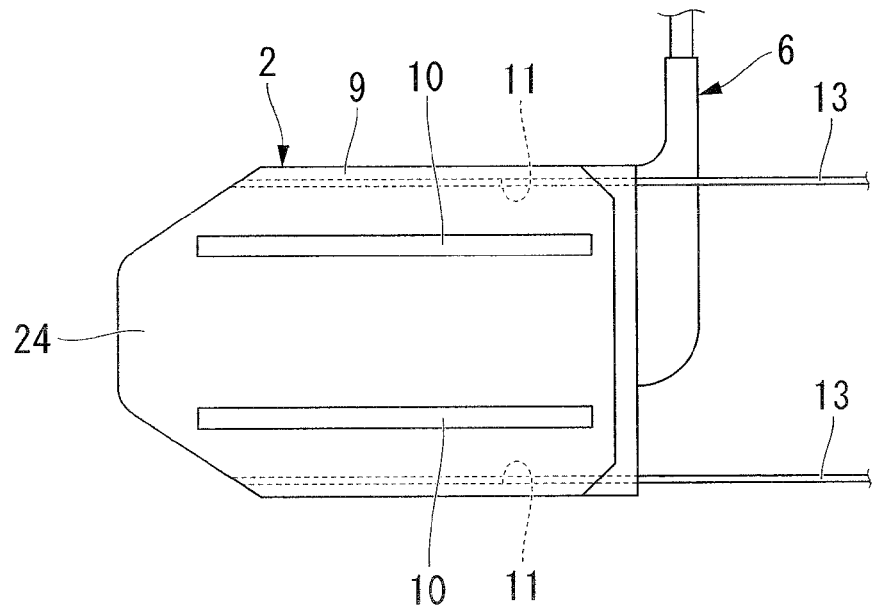
FIG. 18 is a plan view illustrating a state where an electrode unit of an electrode system according to another modified example of the first embodiment of the invention is switched to a stretched shape.

In this embodiment, as shown in FIG. 18, a distal end of the electrode support 9 may be provided with a tapered portion 24 of which the width decreases toward the distal end. Accordingly, it is possible to improve the insertion property at the time of inserting the distal end of the electrode unit 2 between the nerve tissue N and the peripheral tissue M.

Figure 19:
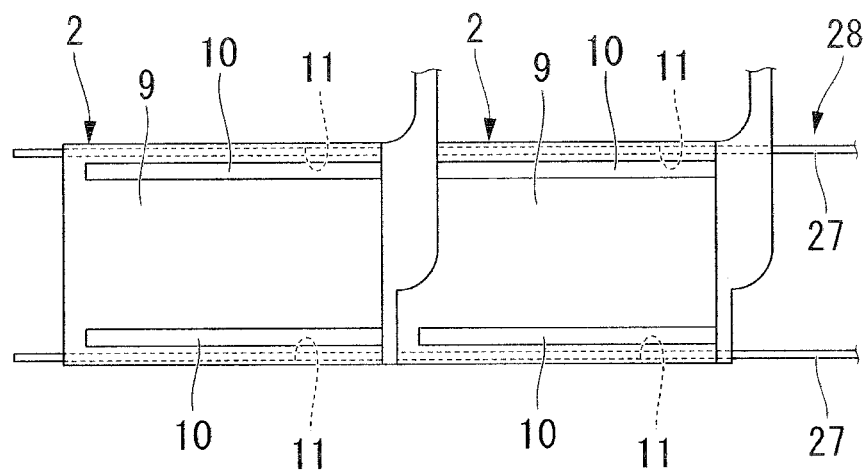
FIG. 19 is a plan view illustrating a state where the stretch member of the treatment tool is inserted through an electrode unit of an electrode system according to another modified example of the first embodiment of the invention.

In this embodiment, as shown in FIG. 19, by providing a treatment tool 28 including stretch members 27 with a length larger than that of the stretch members 13 extending in a predetermined direction instead of the stretch members 13 of the treatment tool 3, a plurality of electrode units 2 may be attached to a pair of stretch members 27 at a time. Accordingly, without pulling out the treatment tool 28 from the trocar T to the outside of the patient's body, it is possible to attach the plurality of electrode units 2 to a linear tissue or the like at a time by the use of the treatment tool 28.

Figure 20:
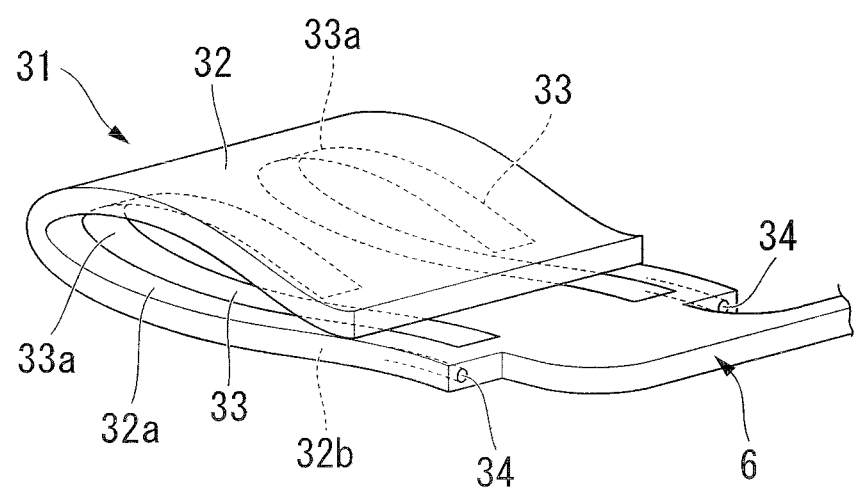
FIG. 20 is a perspective view illustrating an electrode unit of an electrode system according to another modified example of the first embodiment of the invention.

In this embodiment, as shown in FIG. 20, an electrode unit 31 that is folded substantially in half to form a curved shape in which a nerve tissue N is enclosed therein in a natural state where an external force does not act thereon may be provided.

In the modified example, the electrode unit 31 includes an electrode support (insulating member) 32 formed in a sheet shape out of an elastic material and a pair of electrodes 33 formed on the inside surface 32a of the electrode support 32. The electrodes 33 are formed in a plate shape out of an elastic metal material and have bending marks 33a at the center of the electrodes 33 that have a curved shape in a natural state.

In this modified example, guide holes (electrode-side engagement portions) 34 are formed between the inside surface 32a of the electrode support 32 and the outside surface 32b opposite to the inside surface 32a. By forming the guide holes 34 in this way, it is possible to suppress the maximum thickness of the electrode support 32.

Second Embodiment

A second embodiment of the invention will be described below with reference to FIGS. 21 to 24. The same elements as described in the above-mentioned embodiment are identified by the same reference numerals and signs and descriptions thereof are not included herein. Only differences therebetween will be described below.

Figure 21:
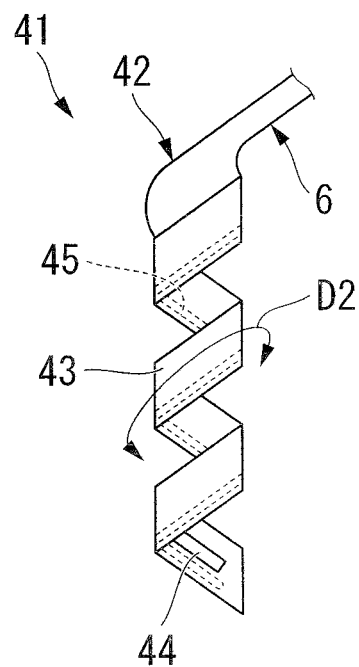
FIG. 21 is a plan view illustrating an electrode unit of an electrode system according to a second embodiment of the invention.

As shown in FIG. 21, an electrode system 41 according to the second embodiment of the invention includes an electrode unit 42 instead of the electrode unit 2 of the electrodes system 1 according to the first embodiment.

The electrode unit 42 is configured in a helical shape to be wound around a nerve tissue N in a predetermined direction in the natural state when an external force does not act thereon.

In this embodiment, the electrode unit 42 includes an electrode support (insulating member) 43 formed in a sheet shape out of an elastic material and a pair of electrodes 44 formed on the inside surface 43a of the electrode support 43.

Figure 22:
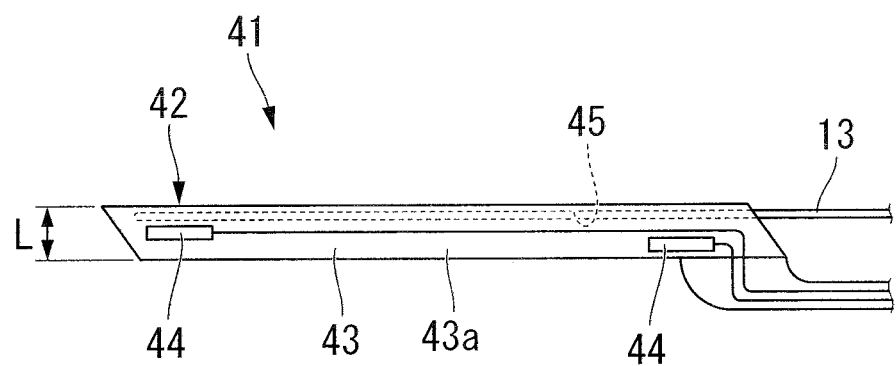
FIG. 22 is a plan view illustrating a state where a stretch member of the treatment tool is inserted through an electrode unit of the electrode system.

Guide holes (electrode-side engagement portions) 45 extending in parallel to a curving direction D2 in which the electrode support 43 is curved in a helical shape are formed in the electrode support 43, and the stretch members 13 are detachably engaged therewith as shown in FIG. 22.

In the electrode system 41 according to this embodiment having the above-mentioned configuration, it is possible to satisfactorily and easily attach the electrode unit 42 to the nerve tissue N.

Since the electrode unit 42 can be wound around the nerve tissue N plural times, it is possible to more satisfactorily attach the electrode unit 42 to the nerve tissue N. It is possible to suppress the width L (see FIG. 22) in the stretched shape of the electrode unit 42 and to reduce the inner diameter of a trocar necessary for passing the electrode unit 42.

Figure 23:
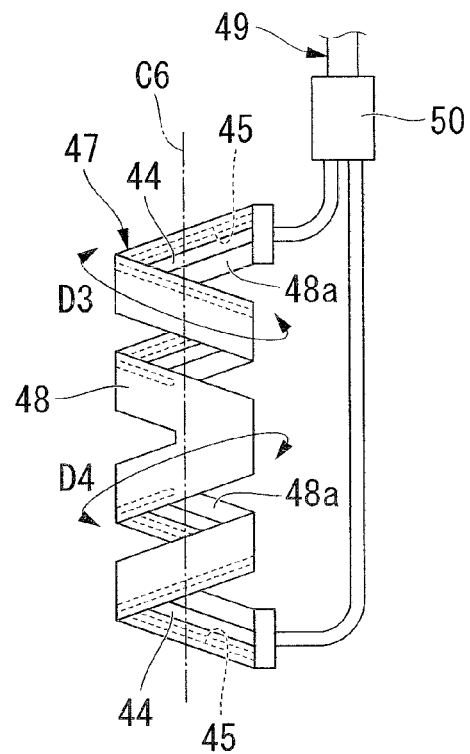
FIG. 23 is a plan view illustrating an electrode unit of an electrode system according to a modified example of the second embodiment of the invention.

In this embodiment, as in the modified example shown in FIG. 23, an electrode unit 47 having a shape in which a portion configured to be wound in a helical shape around a predetermined direction on an axis line C6 of a nerve tissue N and a portion configured to be wound in a helical shape around the opposite direction of the predetermined direction are connected at distal ends thereof in the natural state where an external force does not act thereon may be provided instead of the electrode unit 42. In this embodiment, the electrode unit 47 includes a pair of electrodes 44 and the electrodes 44 are arranged on the inside surface 48a of an electrode support (insulating member) 48 formed substantially in a helical shape to extend in parallel to curving directions D3 and D4. The curving direction D3 and the curving direction D4 are different from each other in a winding direction around the axis line C6.

Figure 24:
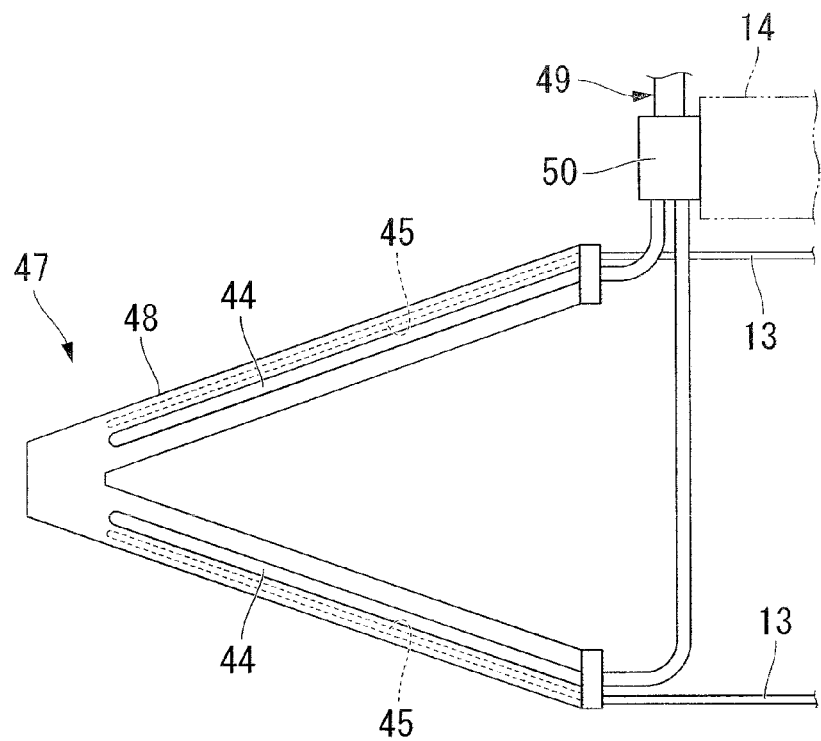
FIG. 24 is a plan view illustrating a state where a stretch member of the treatment tool is inserted through an electrode unit of the electrode system.

When the stretch members 13 are inserted through guide holes 45 of the electrode unit 47, the electrode support 48 is switched to a substantially V-shaped stretched shape as shown in FIG. 24.

In this modified example, the stretch members 13 are separated from the electrode unit 47 in the state where the pressing rod 14 is being brought into contact with a connecting portion 50 formed at the distal end of the lead body 49.

Third Embodiment

A third embodiment of the invention will be described below with reference to FIGS. 25 to 30. The same elements as described in the above-mentioned embodiments are identified by the same reference numerals and signs and descriptions thereof are not included herein. Only differences therebetween will be described below.

Figure 25:
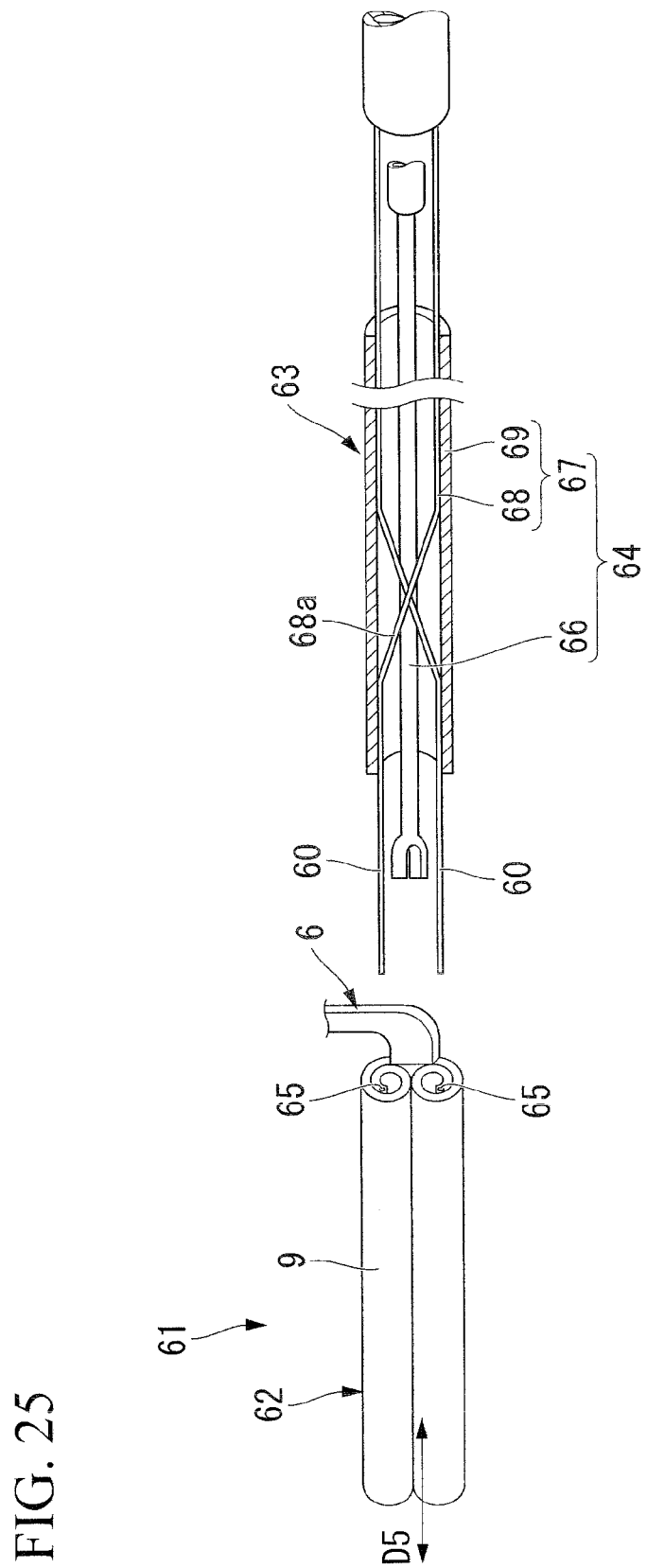
FIG. 25 is a partially exploded plan view illustrating an electrode system according to a third embodiment of the invention.

As shown in FIG. 25, an electrode system 61 according to the third embodiment of the invention includes an electrode unit 62 instead of the electrode unit 2 and includes a treatment tool 63 having a stretch mechanism 64 instead of the treatment tool 3. The electrode unit 62 has a curved shape in the natural state where an external force does not act thereon as shown in FIG. 26.

Figure 26:
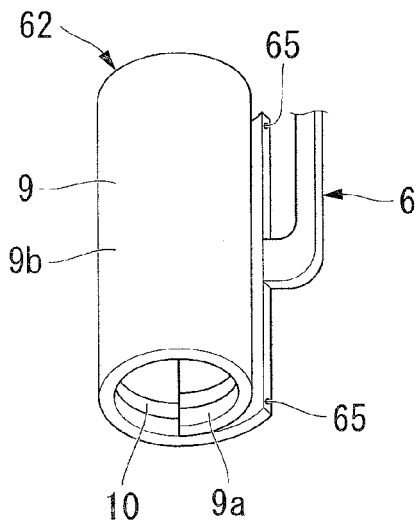
FIG. 26 is a perspective view illustrating an electrode unit of the electrode system in a natural state.
Figure 27:
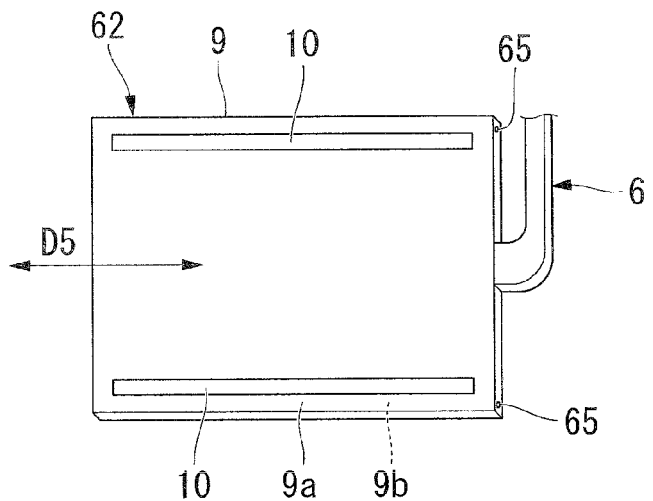
FIG. 27 is a perspective view illustrating a state where the electrode unit has a stretched shape.

As shown in FIGS. 26 and 27, the electrode unit 62 includes a pair of guide holes (electrode-side engagement portions) 65 formed between the first surface 9a and the second surface 9b of the electrode support 9 instead of the guide holes 11 of the electrode unit 2. The lead body 6 is connected to the center of a proximal end of the electrode support 9 in a range narrower than that of the above-mentioned embodiment.

As shown in FIG. 25, the stretch mechanism 64 includes a pair of stretch members 60, a pressing rod (contact member) 66 coming contact with the electrode support 9 at the time of separating the stretch members 60 from the electrode support 9, and a member gap adjusting portion 67 adjusting the gap between the pair of stretch members 60.

The stretch members 60 are members formed substantially in a rod shape out of a metal wire or the like.

The member gap adjusting portion 67 includes a spring member 68 that is fixed to proximal ends of the stretch members 60, that supports the pair of stretch members 60 to extend substantially in parallel with each other, and that can be elastically deformed to adjust the gap between the stretch members 60 to a desired value and a pipe 69 that allows the spring member 68 to pass therethrough so as to regulate the shape of the spring member 68.

The spring member 68 is formed integrally with the stretch members 60 using a metal wire or the like. An intersection 68a where the wires intersect each other in an X shape is provided to the spring member 68. By changing a portion where the inner circumferential surface of a distal end of the pipe 69 comes in contact with the intersection 68a, the gap between the pair of stretch members 60 is also changed.

A process of attaching the electrode unit 62 to a nerve tissue N using the electrode system 61 having the above-mentioned configuration will be described below.

An operator stretches the curved shape of the electrode unit 62 into a stretched shape in which the electrode unit 62 is stretched in a predetermined stretching direction D5 as shown in FIG. 27. The electrode unit 62 having the stretched shape is wound around a predetermined axis line parallel to the stretching direction D5 from both ends as shown in FIG. 25 (shape forming step for introduction).

Figure 28:
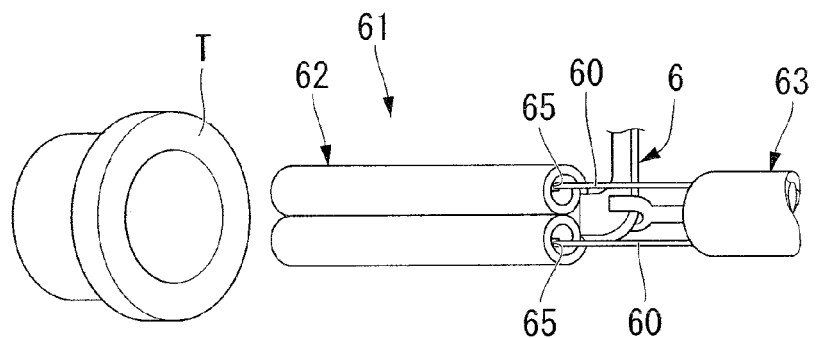
FIG. 28 is a perspective view illustrating a state where a stretch member of a treatment tool is inserted through the electrode unit.

Subsequently, as shown in FIG. 28, the stretch members 60 of which the gap therebetween has been adjusted are inserted into and engaged with the guide holes 65 of the electrode unit 62 in the wound state and the wound shape of the electrode unit 62 is held unchanged. The electrode unit 62 along with the treatment tool 63 is inserted through a trocar T.

Figure 29:
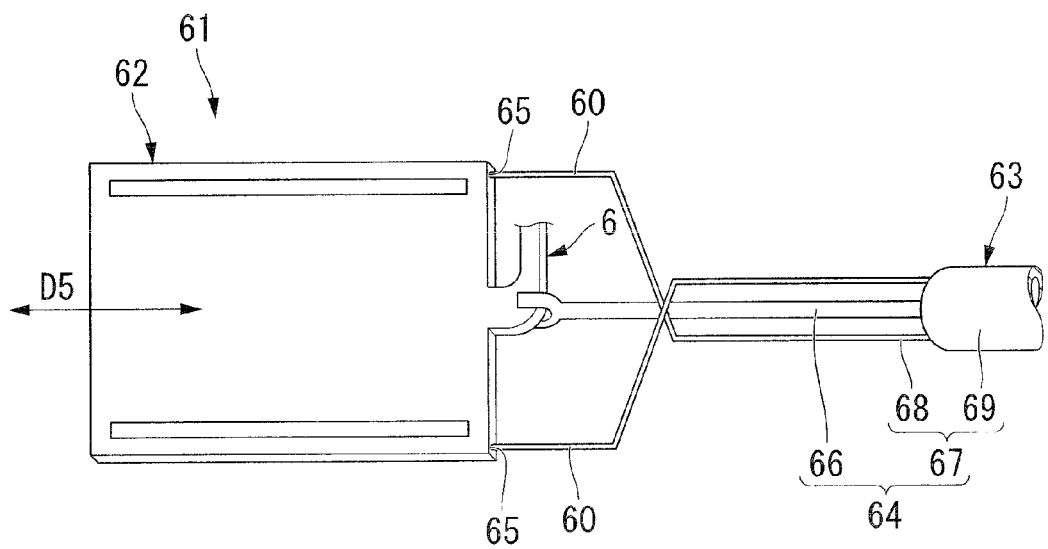
FIG. 29 is a perspective view illustrating a state where the electrode unit is stretched by a stretch member of the treatment tool.

Then, as shown in FIG. 29, by pushing the spring member 68 to the distal end relative to the pipe 69 inside a patient's chest cavity, the electrode unit 62 wound around a predetermined axis line parallel to the stretching direction D5 is unwound and the electrode unit 62 is stretched in a direction perpendicular to the stretching direction D5. At this time, since the stretch members 60 are engaged with the guide holes 65 of the electrode unit 62, the electrode unit 62 has constant rigidity and has a stretched shape.

Figure 30:
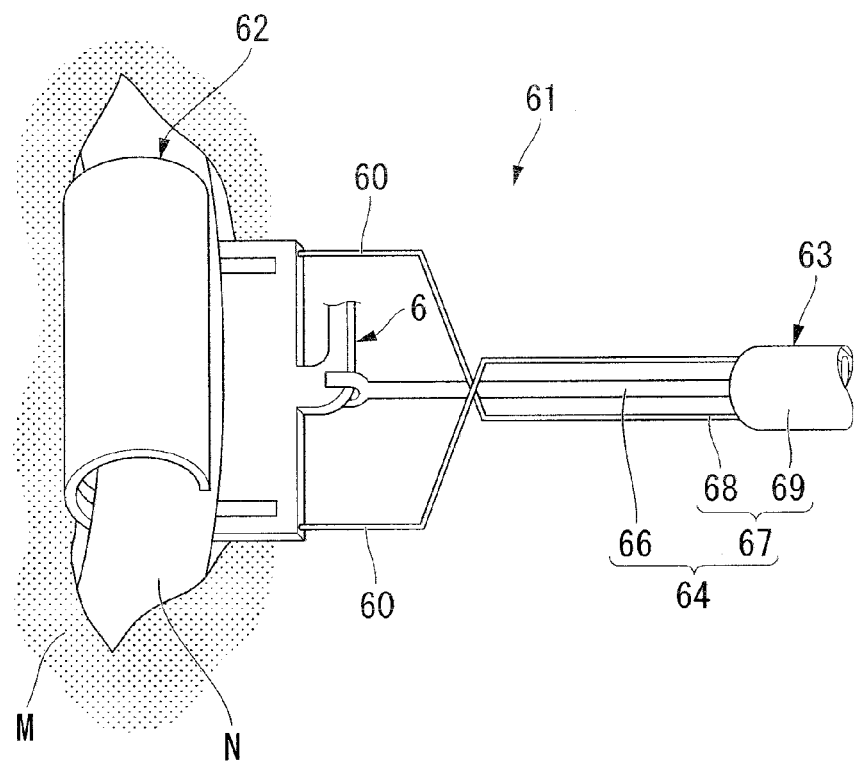
FIG. 30 is a perspective view illustrating a state where the stretch member is detached from the electrode unit.

As shown in FIG. 30, the electrode unit 62 is wound around the nerve tissue N from its distal end by inserting a distal end of the electrode unit 62 between the nerve tissue N and the peripheral tissue M and causing the stretch members 60 to move back relative to the pressing rod 66 while engaging a distal end of the pressing rod 66 with the distal end of the lead body 6.

As described above, in the electrode system 61 according to this embodiment, it is possible to satisfactorily and easily attach the electrode unit 62 to the nerve tissue N.

By inserting the electrode unit 62 through the trocar T in the state where the electrode unit is wound around a predetermined axis line parallel to the stretching direction D5, it is possible to reduce the width of the cross-section in a plane perpendicular to the stretching direction D5 of the electrode unit 62 and to reduce the inner diameter of the trocar T necessary for inserting the electrode unit 62 therethrough, thereby reducing the invasiveness of the procedure to the patient.

Fourth Embodiment

A fourth embodiment of the invention will be described below with reference to FIGS. 31 to 35. The same elements as described in the above-mentioned embodiments are identified by the same reference numerals and signs and descriptions thereof are not included herein. Only differences therebetween will be described below.

Figure 31:
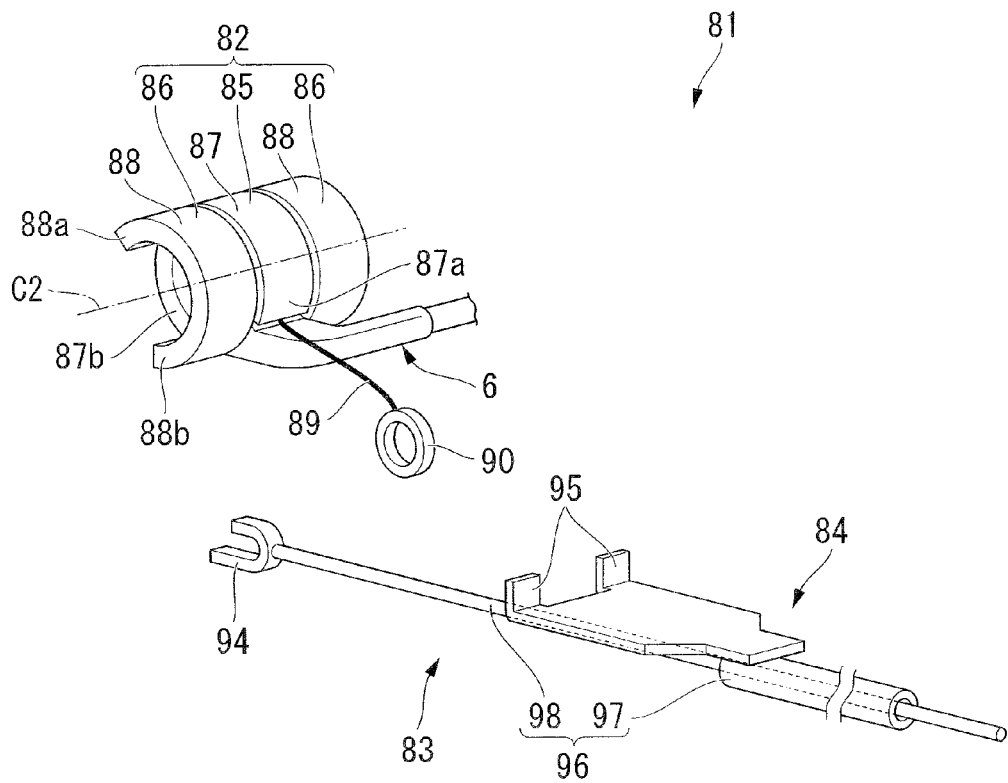
FIG. 31 is a perspective view illustrating an electrode system according to a fourth embodiment of the invention.

As shown in FIG. 31, an electrode system 81 according to the fourth embodiment of the invention includes an electrode unit 82 applying a predetermined voltage to a nerve tissue N and a treatment tool 84 including a stretch mechanism 83 that switches the curved shape of the electrode unit 82 to the stretched shape, maintains the stretched shape, and then releases the stretched shape.

Figure 32:
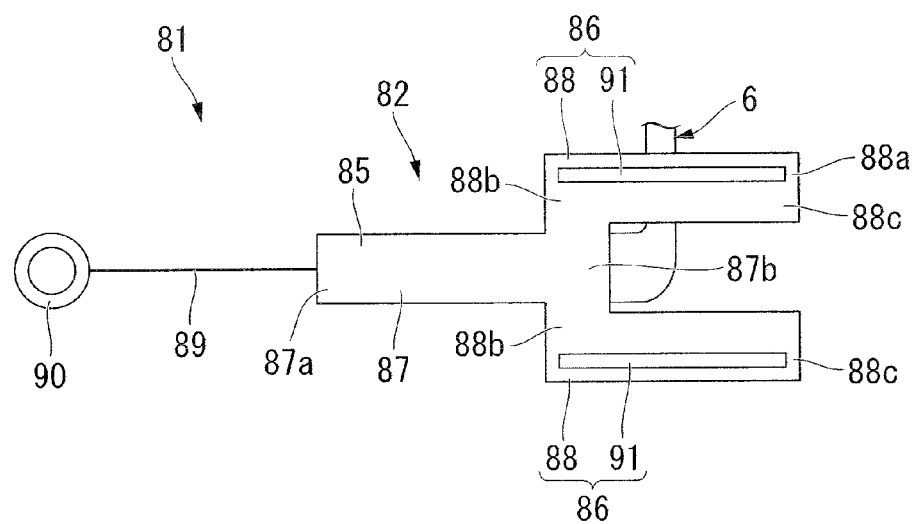
FIG. 32 is a plan view illustrating a state where an electrode unit of the electrode system is stretched into a stretched shape.

As shown in FIGS. 31 and 32, the electrode unit 82 includes a first arm 85 and a second arm 86 that are formed in a curved shape in the natural state where an external force does not act thereon and then can be switched (changed) to a stretched shape. Two second arms 86 are connected to the first arm 85.

The first arm 85 and the second arm 86 include electrode supports (insulating members) 87 and 88, respectively, formed in a sheet shape out of an elastic insulating material.

The electrode support 87 is curved in a first direction around a predetermined axis line C2 from a first end 87a to a second end 87b and the electrode support 88 is curved in a second direction around the axis line C2 from a first end 88a to a second end 88b. The electrode support 88 is disposed on both sides of the electrode support 87 in the direction of the axis line C2. The second end 87b of the electrode support 87 and the second end 88b of the electrode support 88 are integrally formed so that they are connected to each other.

The electrode support 87 has a shape in which it is curved around the axis line C2 by one turn, but the electrode support 88 has a shape in which it is curved around the axis line C2 by about a half turn.

A first end of a flexible string-like member 89 is connected to the first end 87a of the electrode support 87 and a second end of the string-like member 89 is connected to a ring-like introduction portion 90.

The second arm 86 includes electrodes 91 electrically connected to the nerve stimulator 5 through the lead body 6. The electrodes 91 are disposed on the inside surface 88c when the electrode support 88 has a curved shape.

As shown in FIG. 31, the stretch mechanism 83 includes a towing hook (first end holding portion) 94 that is formed substantially in a J shape and is engaged with the introduction portion 90 to support the first end (87a) of the first arm 85, a pair of claws (second end engaging portion) 95 that are engaged with the second end 87b of the first arm 85, and a gap adjusting mechanism 96 that adjusts the gap between the towing hook 94 and the pair of claws 95.

The gap adjusting mechanism 96 includes a body 97 formed substantially in a tubular shape and a sliding member 98 that is formed in a rod shape and is inserted through the body 97 so as to slide.

The towing hook 94 is fixed to a distal end of the sliding member 98 and the pair of claws 95 is fixed to a distal end of the body 97.

A process of attaching the electrode unit 82 to a nerve tissue N using the electrode system 81 having the above-mentioned configuration will be described below.

Figure 33:
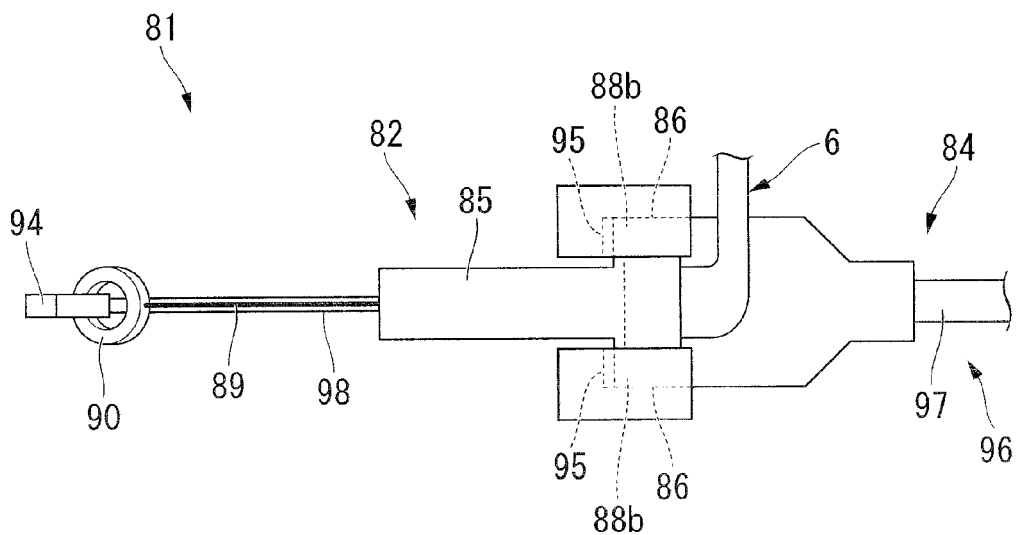
FIG. 33 is a plan view illustrating a state where the electrode unit is attached to a treatment tool of the electrode system.
Figure 34:
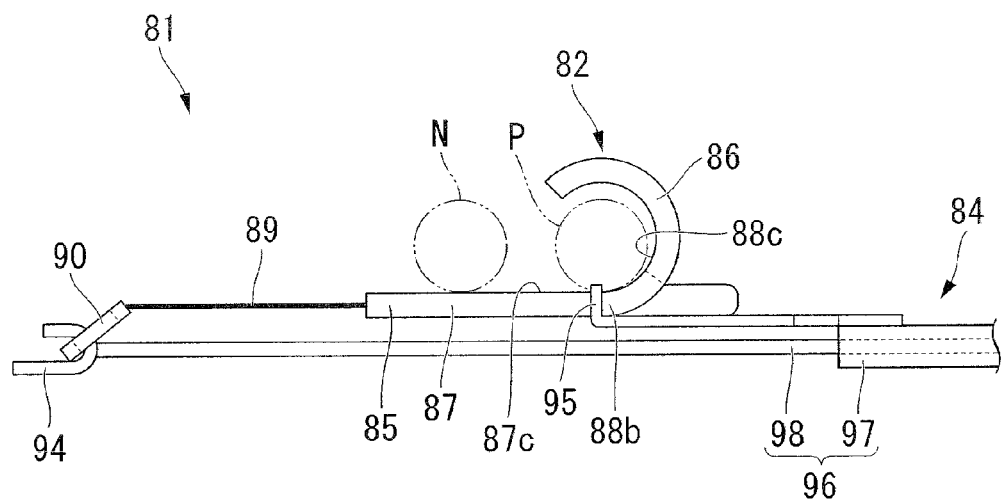
FIG. 34 is a side view illustrating a state where the electrode unit is attached to the treatment tool.

As shown in FIGS. 33 and 34, an operator engages the towing hook 94 with the introduction portion 90 of the electrode unit 82 and holds the engagement, and engages the claws 95 to the second end 88b of the second arm 86. By moving the sliding member 98 to the distal end relative to the body 97 and increasing the gap between the towing hook 94 and the pair of claws 95, the first arm 85 having the curved shape is stretched and held in the stretched shape.

Then, the operator inserts the electrode unit 82 along with the treatment tool 84 through a trocar not shown.

As shown in FIG. 34, the operator operates the treatment tool 84 inside a patient's chest cavity so as to oppose the inside surface 87c of the electrode support 87 to the nerve tissue N. Here, when the sliding member 98 moves toward the proximal end while fixing the position of the body 97, the first arm 85 is returned to the curved shape, whereby the nerve tissue N is shifted to a position P surrounded with the second arm 86.

Figure 35:
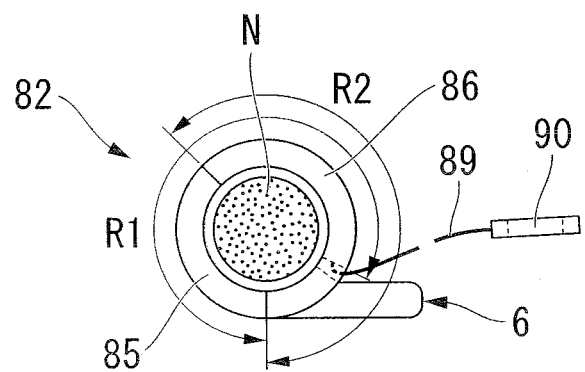
FIG. 35 is a sectional view illustrating a state where the electrode unit is attached to a nerve tissue.

As shown in FIG. 35, the first arm 85 is wound around the nerve tissue N within the range R1 and the second arm 86 is wound around the nerve tissue within the range R2. As needed, the introduction portion 90 may be towed with a forceps or the like not shown to assist in winding the first arm 85 around the nerve tissue N.

The operator cuts the string-like member 89 with a cutting tool not shown introduced through the trocar and separates the electrode unit 82 wound around the nerve tissue N from the treatment tool 84.

As described above, in the electrode system 81 according to this embodiment, it is possible to satisfactorily and easily attach the electrode unit 82 to the nerve tissue N.

In this embodiment, instead of providing the string-like member 89 and the introduction portion 90 to the electrode unit 82, a through-hole may be formed at the first end 87a of the insulating member 87 and this through-hole may be engaged with the towing hook 94.

In the electrode unit 82, by arranging the first arms 85 on both sides of the axis line of the second arm 86 and forming the second end 88b of the electrode support 88 and the second end 87b of the electrode support 87 integrally, the first arms 85 may be connected to the second arm 86.

Fifth Embodiment

A fifth embodiment of the invention will be described below with reference to FIGS. 36 to 40. The same elements as described in the above-mentioned embodiments are identified by the same reference numerals and signs and descriptions thereof are not included herein. Only differences therebetween will be described below.

Figure 36:
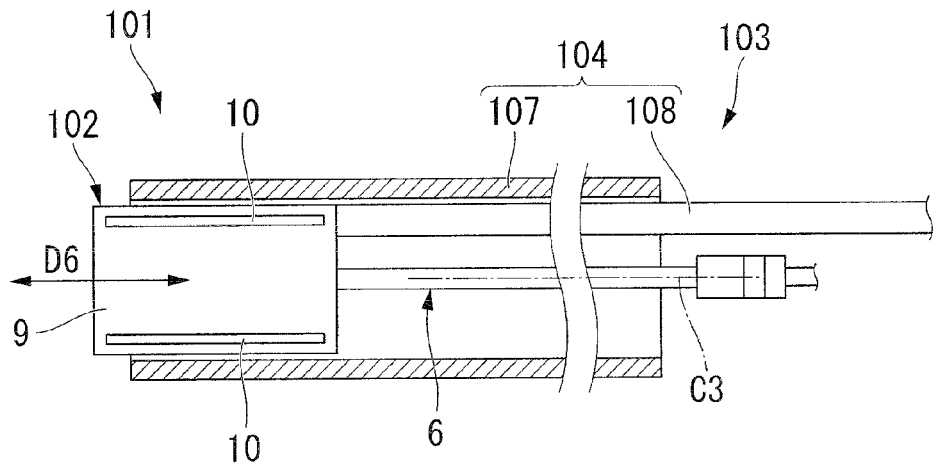
FIG. 36 is a sectional plan view illustrating an electrode system according to a fifth embodiment of the invention.
Figure 37:
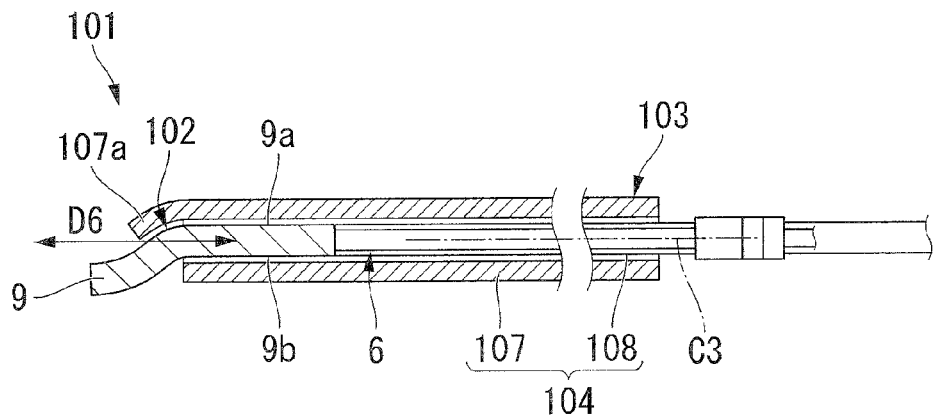
FIG. 37 is a side sectional view of the electrode system.

As shown in FIGS. 36 and 37, an electrode system 101 according to the fifth embodiment of the invention includes an electrode unit 102 applying a predetermined voltage to a nerve tissue N and a treatment tool 103 used to attach the electrode unit 102 to the nerve tissue N.

The electrode unit 102 is different from the electrode 2 according to the above-mentioned embodiment, in that the guide holes 11 are not formed in the electrode unit.

The treatment tool 103 according to this embodiment includes a stretch mechanism 104 that pinches the electrode unit 102 from the first surface 9a and the second surface 9b of the electrode support 9 and holds the electrode unit 102 in the stretched shape and that releases the pinching, instead of the stretch mechanism 12 of the treatment tool 3 according to the above-mentioned embodiment.

The stretch mechanism 104 includes a pipe (tubular member) 107 that receives the electrode unit 102, of which the curved shape has been stretched in an electrode-unit stretching direction D6, therein so as to cause the electrode-unit stretching direction D6 to be parallel to the direction of its axis line C3 and an extruding rod (extrusion member) 108 that extrudes the electrode unit 102 in the pipe 107 toward a distal end in the direction of the axis line C3.

The cross-section of the pipe 107 in a plane perpendicular to the axis line thereof has a flat crushed shape. A guide portion 107a curving the electrode unit 102 toward the axis line C3 as it goes closer to the distal end is formed on a distal end of the pipe 107 where the electrode unit 102 is curved.

Figure 38:
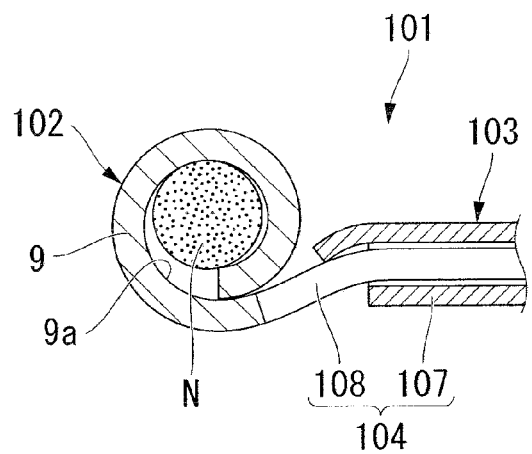
FIG. 38 is a sectional view illustrating a state where an electrode unit of the electrode system is attached to a nerve tissue.

A process using the electrode system 101 having the above-mentioned configuration is carried out in the following order. An operator operates the treatment tool 103 to extrude the extruding rod 108 to the distal end while fixing the position of the pipe 107 as shown in FIG. 38 in the state where the first surface 9a of the electrode support 9 is disposed to face the nerve tissue N. Then, since the electrode unit 102 is received in the pipe 107 in the state where the electrode-unit stretching direction D6 is parallel to the direction of the axis line C3 of the pipe 107, the portion of the electrode unit 102 protruding from the distal end of the pipe 107 is curved around a predetermined direction perpendicular to the axis line C3 and is wound around the nerve tissue N.

As described above, in the electrode system 101 according to this embodiment, it is possible to satisfactorily and easily attach the electrode unit 102 to the nerve tissue N.

The shape of the electrode unit 102 can be switched by receiving the electrode unit 102 stretched in the electrode-unit stretching direction D6 in the pipe 107, thereby more easily carrying out the process.

Sixth Embodiment

A sixth embodiment of the invention will be described below with reference to FIGS. 39 to 41. The same elements as described in the above-mentioned embodiments are identified by the same reference numerals and signs and descriptions thereof are not included herein. Only differences therebetween will be described below.

Figure 39:
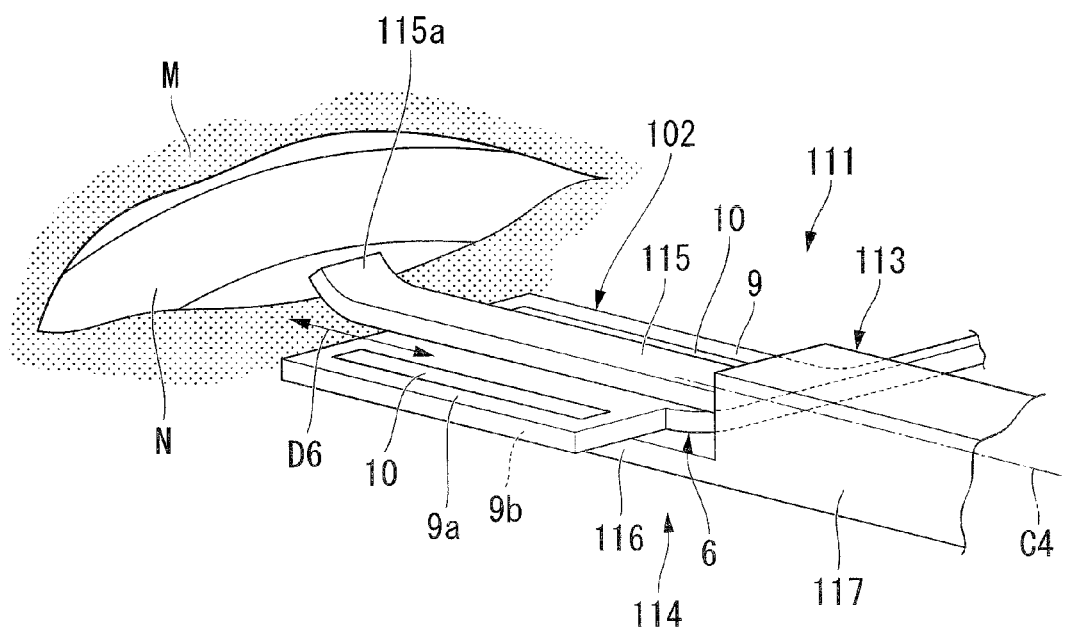
FIG. 39 is a perspective view illustrating an electrode system according to a sixth embodiment of the invention.

As shown in FIG. 39, a treatment tool 113 of an electrode system 111 according to the sixth embodiment of the invention includes a stretch mechanism 114 instead of the stretch mechanism 104 of the treatment tool 103 of the electrode system 101 according to the fifth embodiment.

Figure 40:
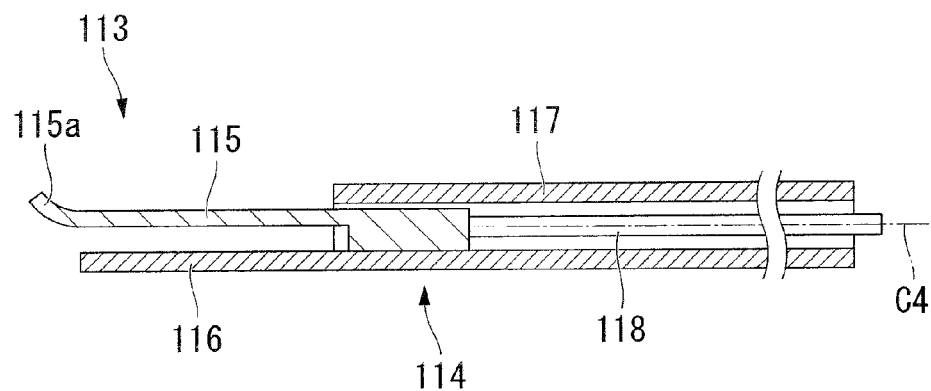
FIG. 40 is a side sectional view illustrating a treatment tool of the electrode system.

As shown in FIGS. 39 and 40, the stretch mechanism 114 includes a first spatula-like member (first pinch member) 115 that is disposed on the side of the first surface 9a of electrode support 9 and that is movable toward a proximal end of the treatment tool 113, a second spatula-like member (second pinch member) 116 that is disposed on the side of the second surface 9b of the electrode support 9, and a pipe (support member) 117 that comes in contact with the proximal end of the electrode support 9.

The second spatula-like member 116 is disposed substantially in parallel to the pipe 117 and is formed integrally with the pipe 117, whereby the proximal end thereof is connected to the distal end of the pipe 117.

The first spatula-like member 115 is disposed at a position opposed to the second spatula-like member 116 with a predetermined gap therebetween and is movable in the direction of the axis line C4 of the pipe 117. A guide portion 115a formed to go apart from the second spatula-like member 116 as it goes closer to the distal end is formed at a distal end of the first spatula-like member 115. A proximal end of the first spatula-like member 115 is connected to a distal end of an operation rod 118 slidably inserted through the pipe 117.

A process using the electrode system 111 having the above-mentioned configuration is carried out in the following order.

As shown in FIG. 39, an operator places the electrode unit 102 between the first spatula-like member 115 and the second spatula-like member 116, pinches the electrode unit 102 between the first spatula-like member 115 and the second spatula-like member 116 to switch the shape of the electrode unit to the stretched shape. At this time, it is preferable that the electrode unit 102 is pinched so that the direction of the axis line C4 in which the first spatula-like member 115 moves is parallel to the electrode-unit stretching direction D6 in which the curvature of the electrode unit 102 is stretched and extended. Then, the operator inserts the electrode unit 102 along with the treatment tool 113 through a trocar not shown.

Subsequently, the operator cuts the peripheral tissue M with a knife not shown or the like to expose the nerve tissue N. At this time, by bringing the guide portion 115a formed at the distal end of the first spatula-like member 115 into contact with the nerve tissue N and drawing out the nerve tissue N, it is possible to easily expose the nerve tissue N from the peripheral tissue M.

Then, the operator operates the treatment tool 113 to move the operation rod 118 toward a proximal end of the operation rod 118 while fixing the position of the pipe 117 in the state where the first surface 9a of the electrode support 9 faces the nerve tissue N, whereby the first spatula-like member 115 is retreated.

Figure 41:
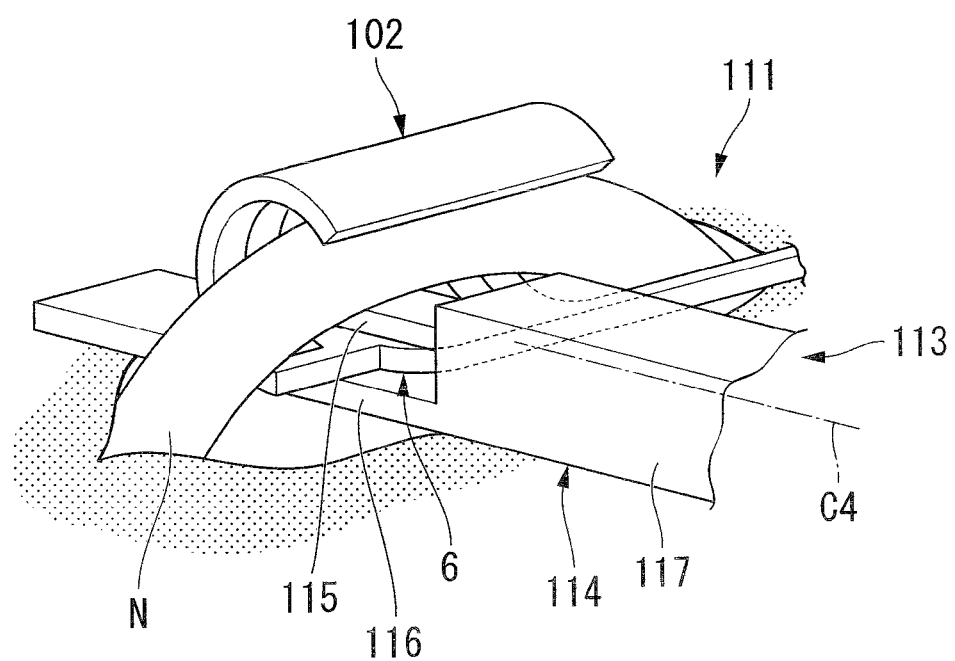
FIG. 41 is a perspective view illustrating a state where an electrode unit of the electrode system is attached to a nerve tissue.

Then, since the electrode unit 102 is pinched between the first spatula-like member 115 and the second spatula-like member 116 so that the electrode-unit stretching direction D6 is parallel to the direction of the axis line C4 of the pipe line 117, the portion of the electrode unit 102 protruding from the distal end of the first spatula-like member 115 is curved around a predetermined direction perpendicular to the axis line C4 and is wound around the nerve tissue N, as shown in FIG. 41.

As described above, in the electrode system 111 according to this embodiment, it is possible to satisfactorily and easily attach the electrode unit 102 to the nerve tissue N.

Since the electrode unit 102 is pinched between the first spatula-like member 115 and the second spatula-like member 116, it is possible to more easily switch the shape of the electrode unit 102 by attaching the electrode unit 102 to the treatment tool 113.

Seventh Embodiment

A seventh embodiment of the invention will be described below with reference to FIGS. 42 to 46. The same elements as described in the above-mentioned embodiments are identified by the same reference numerals and signs and descriptions thereof are not included herein. Only differences therebetween will be described below.

Figure 42:
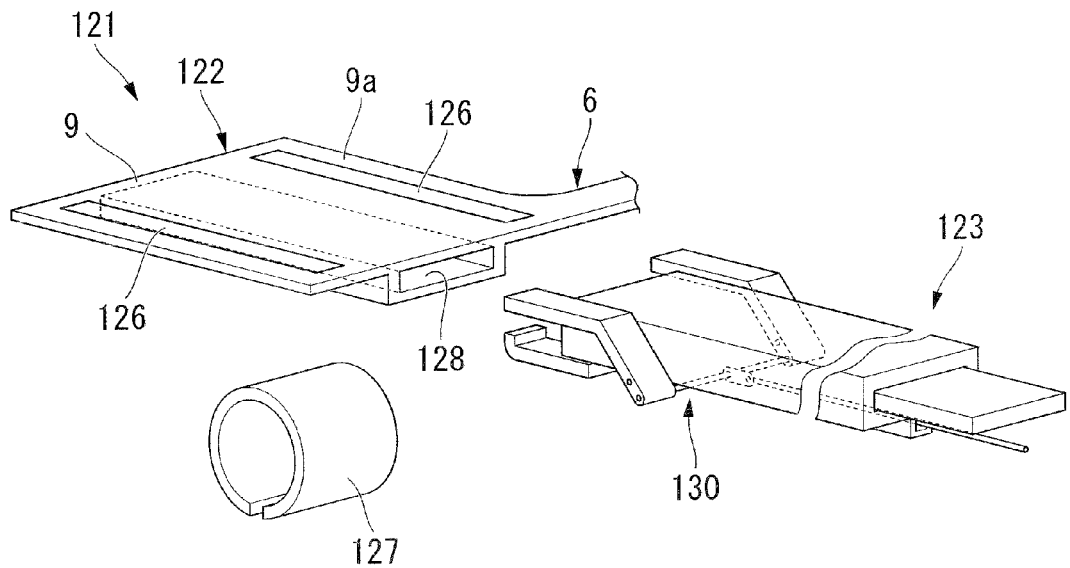
FIG. 42 is a perspective view illustrating an electrode system according to a seventh embodiment of the invention.

As shown in FIG. 42, an electrode system 121 according to the seventh embodiment of the invention includes an electrode unit 122 applying a predetermined voltage to a nerve tissue N and a treatment tool 123 used to attach the electrode unit 122 to the nerve tissue N.

The electrode unit 122 is formed in a stretched shape in the natural state where an external force does not act thereon and can switch (change) its shape to a curved shape where it is curved to be wound around the nerve tissue N.

The electrode unit 122 includes the electrode support 9 according to the above-mentioned embodiment, a pair of electrodes 126 formed in the first surface 9a which is the inside surface of the curvature formed by the electrode support 9 having the curved shape, and a curving member 127 formed in the curved shape out of an elastic material having higher rigidity than that of the electrode support 9 so as to be wound around the nerve tissue N.

The electrodes 126 are different from the electrode 10, in that the electrodes 126 are formed in a stretched shape in the state where an external force does not act thereon and can be deformed by their elasticity.

A guide hole (electrode-side engagement portion) 128 extending in parallel to the first surface 9a and passing through the electrode support 9 is formed in the electrode support 9 according to this embodiment, instead of the pair of guide holes 11 according to the above-mentioned embodiment. The curving member 127 can be inserted through and engaged with the guide hole 128.

The treatment tool 123 includes a curving mechanism 130 switching the stretched shape of the electrode unit 122 in the natural state to the curved shape.

Figure 43:
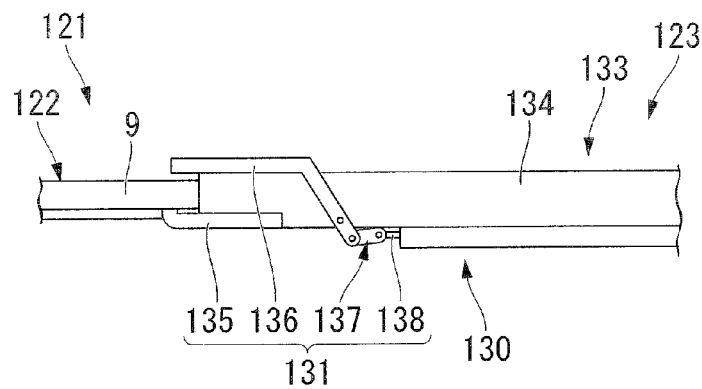
FIG. 43 is a side view illustrating a state where a treatment tool of the electrode system is attached to an electrode unit.
Figure 44:
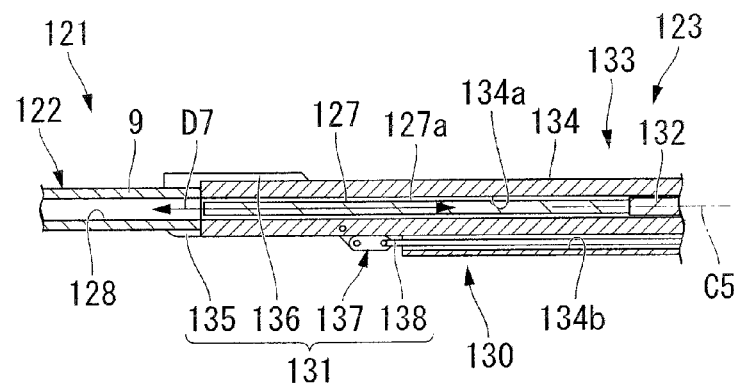
FIG. 44 is a side sectional view illustrating a state where the treatment tool is attached to the electrode unit.

As shown in FIGS. 43 and 44, the curving mechanism 130 includes a grasp portion 131 grasping the electrode support 9, a reinforcing member 132 that is formed to extend in a predetermined direction with constant rigidity and is detachably engaged with the guide hole 128 of the electrode support 9, and an extruding portion 133 that holds the curving member 127 in a stretched state and extrudes the stretched curving member 127.

In this embodiment, the reinforcing member 132 forms a part of the extruding member 133.

The extruding portion 133 includes a pipe 134 holding the curving member 127 in a state where it is stretched in a curving-member stretching direction D7 in which the curvature of the curving member 127 is stretched and the reinforcing member 132 extruding the curving member 127, which has been stretched in the curving-member stretching direction D7, in the curving-member stretching direction D7.

The reinforcing member 132 is inserted through a through-hole 134a formed in the pipe 134 so as to slide relative to the pipe 134.

The grasp portion 131 includes a fixing member 135 fixed to the vicinity of the opening of a distal end of the pipe 134, a moving member 136 movable to a predetermined position, a known link mechanism 137 of which a first end is connected to the moving member 136, and an operation rod 138 connected to a second end of the link mechanism 137.

By the link mechanism 137, the moving member 136 can move between a position opposed to the fixing member 135 so as to pinch the electrode support 9 therebetween and a position separated from the fixing member 135.

The operation rod 138 is slidably inserted through an auxiliary hole 134b formed in parallel to the through-hole 134a in the pipe 134, grasps the proximal end of the electrode support 9 with the fixing member 135 and the moving member 136 when the operation rod 138 is towed from the pipe 134, and releases the grasping of the electrode support 9 when the operation rod 138 is pushed into the pipe 134.

A process of attaching the electrode unit 122 to the nerve tissue N using the electrode system 121 having the above-mentioned configuration will be described below.

An operator inserts and engages the reinforcing member 132 through and with the guide hole 128 of the electrode unit 122 and inserts the electrode unit 122 and the treatment tool 123 through a trocar not shown.

Figure 45:
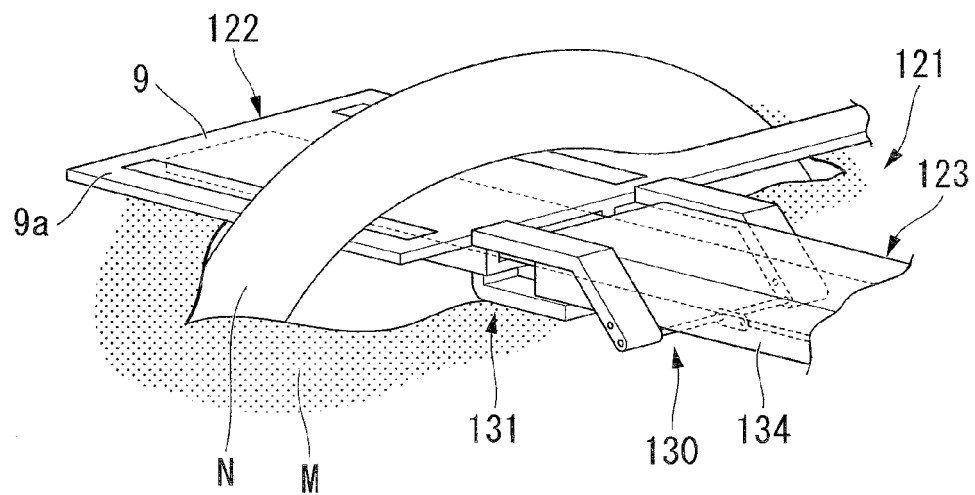
FIG. 45 is a diagram illustrating a state where the electrode unit is inserted between a nerve tissue and a membrane.

Since the reinforcing member 132 is inserted through the guide hole 128, the electrode unit 122 having the stretched shape has constant rigidity. Accordingly, as shown in FIG. 45, it is possible to easily insert the electrode unit 122 between the nerve tissue N and the peripheral tissue M. At this time, the electrode unit is inserted so that the nerve tissue N is disposed on the first surface 9a of the electrode unit 122.

Subsequently, the reinforcing member 132 is towed from a proximal end of the pipe 134 to separate the reinforcing member 132 from the electrode unit 122 and the pipe 134, in the state where the electrode support 9 is grasped by the grasp portion 131. As shown in FIG. 44, the curving member 127 of which the curvature is stretched in the curving-member stretching direction D7 is inserted into the through-hole 134a so that the curving-member stretching direction D7 is parallel to the axis line C5 of the pipe 134, and the reinforcing member 132 is inserted into the through-hole 134a again from a proximal end of the curving member 127. At this time, the curving member 127 is inserted into the through-hole 134a so that the nerve tissue N is located on the inside surface 127a of the curving member 127 in the curved shape.

Figure 46:
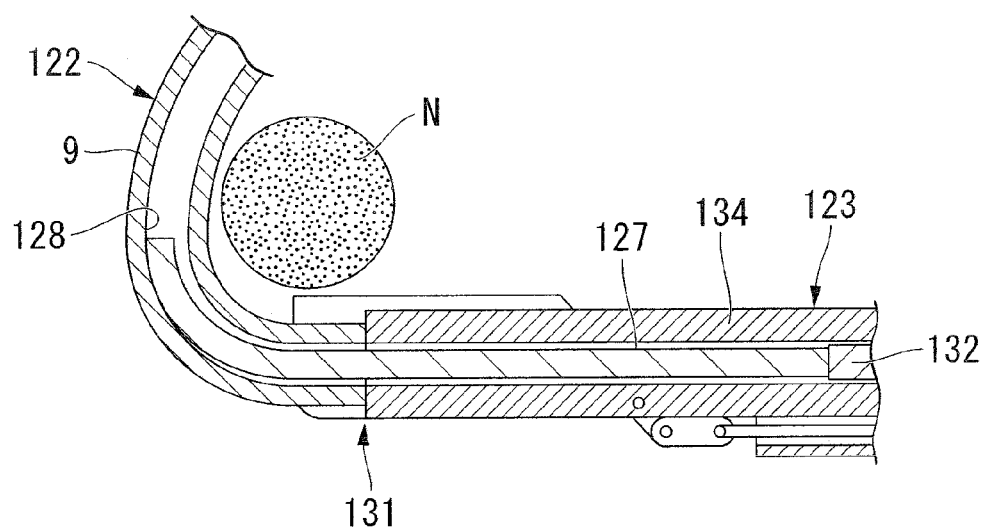
FIG. 46 is a sectional view illustrating a state where the electrode unit is attached to a nerve tissue.

Here, when the reinforcing member 132 is pushed into the pipe 134, the curving member 127 is inserted into the guide hole 128 of the electrode unit 122 as shown in FIG. 46. Since the curving member 127 is formed of an elastic material having higher rigidity than that of the electrode support 9, the curving member 127 protruding from the distal end of the pipe 134 is returned to the curved shape and changes the shape of the electrode support 9 to the curved shape.

When the insertion of the curving member 127 into the guide hole 128 of the electrode unit 122 is finished, the operator pushes the operation rod 138 into the pipe 134 to release the grasping of the electrode support 9 by the grasp portion 131 and separates the treatment tool 123 from the electrode unit 122.

As described above, in the electrode system 121 according to this embodiment, it is possible to satisfactorily and easily attach the electrode unit 122 to the nerve tissue N.

Although the first to seventh embodiments of the invention have been described in detail with reference to the drawings, the specific configuration is not limited to the embodiments, but may include modifications in configuration without departing from the concept of the invention.

In the first to seventh embodiments, for example, the part which can be switched between the curved shape and the stretched shape is the entire electrode unit, but the part which can be switched in shape may be only a part of the electrode unit.

Although it has been described in the first to seventh embodiments that the shape of the electrode unit can be switched between the curved shape and the stretched shape by means of the elastic force of the electrode, the shape may be switched by means of the elastic force of the electrode support. The electrode unit may include a hyperelastic body such as a shape-memory alloy and the elastic force for deforming the electrode unit may be generated by the hyperelastic body. However, since the electrode support can be more easily produced in the stretched shape in the natural state, the elastic force for changing the shape of the electrode unit is preferably generated from the electrode or the hyperelastic body.

In the first to seventh embodiments, the guide hole as the electrode-side engagement portion is a through-hole. However, the shape of the electrode-side engagement portion is not limited to the through-hole, but may be any as long as it can be engaged with the stretch member. For example, the electrode-side engagement portion may have a groove shape in which a notch is formed in the stretch direction.

Although it has been described in the first to seventh embodiments that a nerve tissue is exemplified as the linear tissue, the linear tissue is not limited to the nerve tissue, but may be a blood vessel, an alimentary canal, or a muscle.

Eighth Embodiment

An embodiment of an electrode implanting system according to the invention will be described below with reference to FIGS. 47 to 64. In the following embodiment, it is assumed that the electrode implanting system is medically used along with a forceps.

Figure 47:
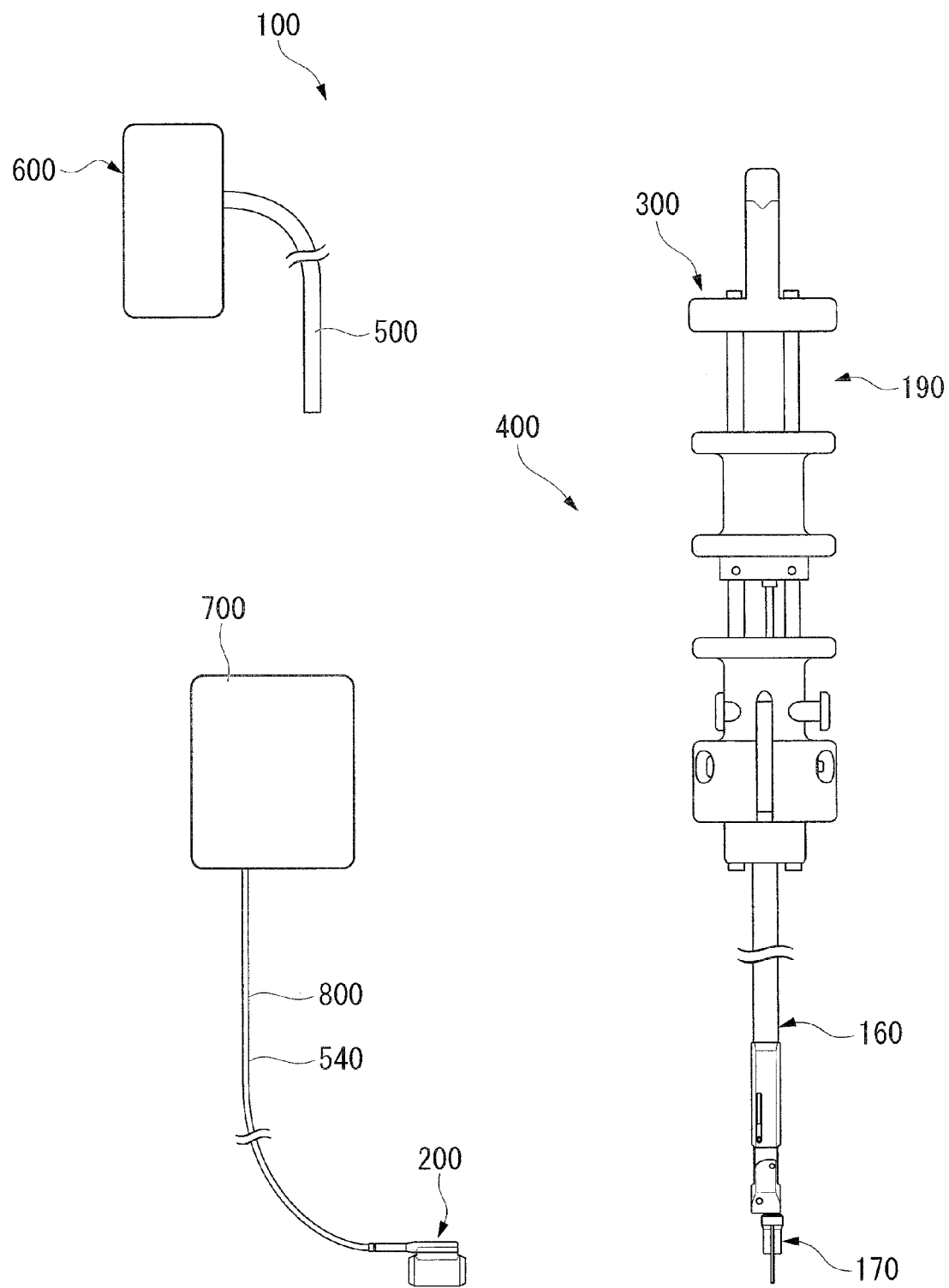
FIG. 47 is a diagram illustrating the entire configuration of an electrode implanting system according to an embodiment of the invention.

As shown in FIG. 47, the electrode implanting system 100 according to an eighth embodiment of the invention includes an electrode implanting apparatus 400 including an electrode unit 200 that is formed in a curved shape to be wound around a nerve tissue (linear tissue) in the natural state where an external force does not act thereon and a treatment tool 300 that switches the shape of the electrode unit 200 from the curved shape to the stretched shape and a thoracoscope (observation apparatus) 600 having a long observation insertion section 500.

In this embodiment, the electrode implanting system 100 is used along with a nerve stimulator 700 generating an electrical stimulus to be applied to the nerve tissue and a lead body 800 electrically connecting the electrode unit 200 to the nerve stimulator 700.

Figure 48:
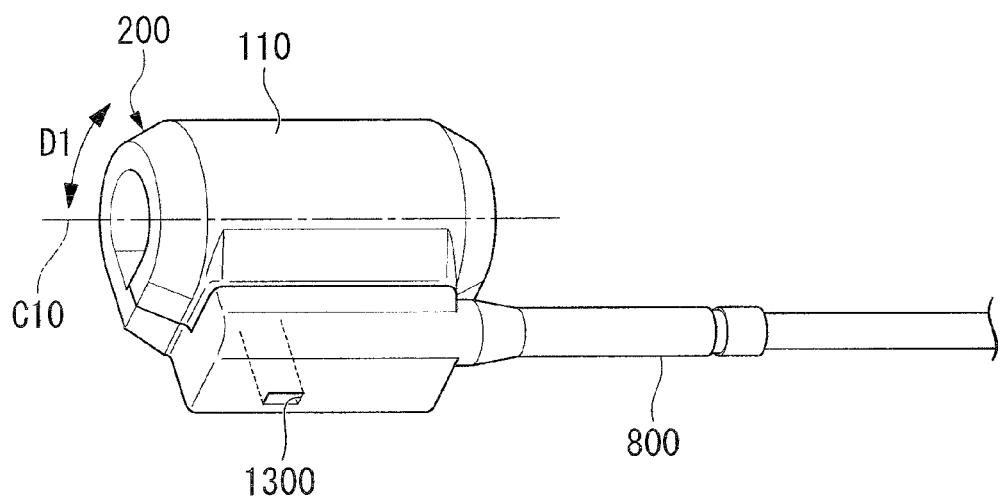
FIG. 48 is a perspective view illustrating an electrode unit of the electrode implanting system in a natural state where an external force does not act thereon.
Figure 49:
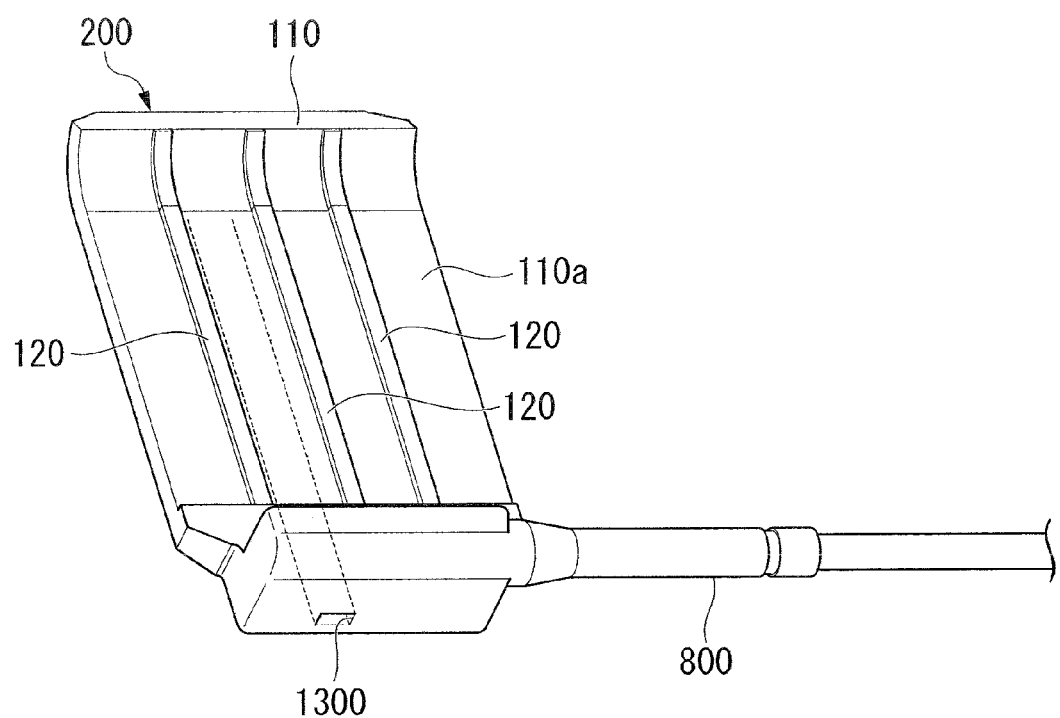
FIG. 49 is a perspective view illustrating a state where a curvature of the electrode unit is stretched into a stretched shape.

The entire shape of the electrode unit 200 can be switched (deformed) from the curved shape in which it is curved to be wound around the nerve tissue in the natural state as shown in FIG. 48 to the stretched shape shown in FIG. 49.

As shown in FIG. 49, the electrode unit 200 includes an electrode support (insulating member) 110 formed in a sheet shape out of an elastic material and three electrodes 120 formed to be exposed from a first surface 110a which is the inside surface of the curvature when the electrode support 110 is curved.

The electrode support 110 is formed of a soft insulating material such as silicone so as not to damage the nerve tissue.

A guide hole (electrode-side engagement portion) 1300 which is a through-hole having a rectangular cross-section is formed in the electrode support 110. The guide hole 1300 is formed at the center in the thickness direction of the electrode support 110 so as to extend in parallel to the curving direction D1 in which the electrode support 110 is curved. In the guide hole 1300, only an end of the electrode support 110 connected to the lead body 800 is opened.

Three electrodes 120 are formed to extend in parallel to the curving direction D1 with intervals therebetween in the direction of the axis line C10 of the curvature when the electrode support 110 is curved. The electrodes 120 are formed of a metal or the like having elasticity and high biocompatibility and have a curved shape in the natural state. That is, the electrode unit 200 has the curved shape in the natural state with the elastic force of the electrodes 120 and can be deformed into the stretched shape. Metal such as platinum or iridium having high biocompatibility can be preferably used as the material of the electrodes 120.

Figure 50:
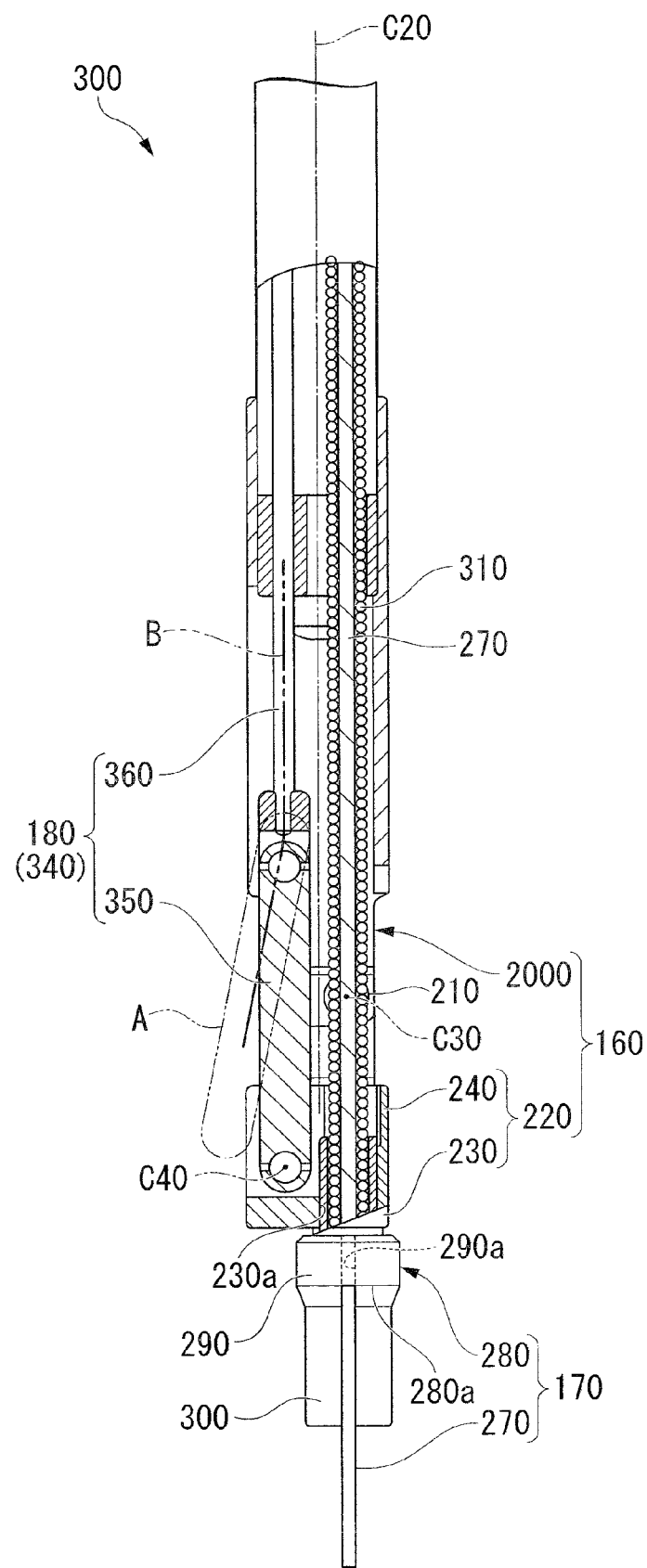
FIG. 50 is a partial sectional view illustrating a distal end of a treatment tool of the electrode implanting system.

As shown in FIGS. 47 and 50, the treatment tool 300 includes a long insertion section 160, a stretch mechanism 170 that is disposed at a distal end of the insertion section 160 so as to hold the electrode unit 200, an adjusting mechanism 180 that adjusts the direction of the electrode unit 200 held by the stretch mechanism 170, and an operation unit 190 that is disposed at a proximal end of the insertion section 160 so as to operate the stretch mechanism 170 and the adjusting mechanism 180.

Figure 51:
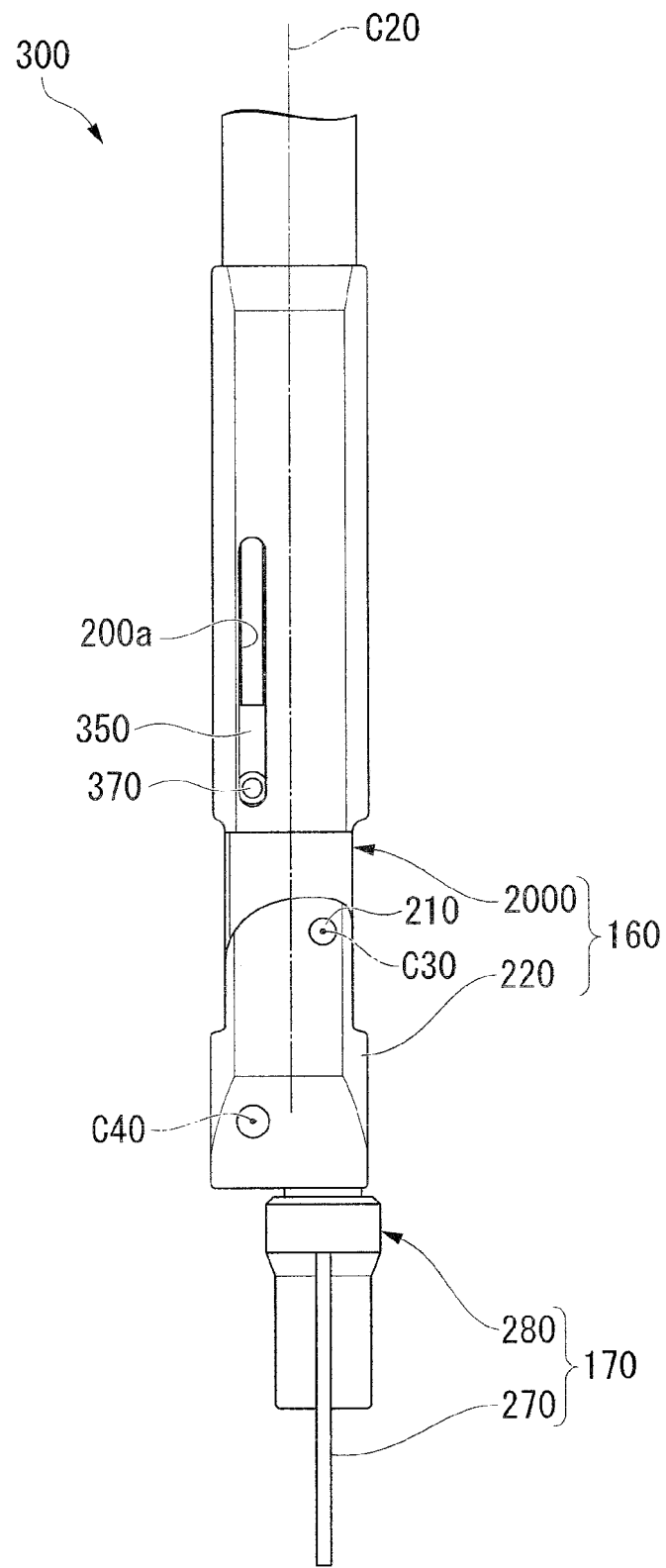
FIG. 51 is a front view illustrating the distal end of the treatment tool of the electrode implanting system.

As shown in FIGS. 50 and 51, the insertion section 160 includes an insertion section body 2000 that is formed in a long tubular shape and a rotating member 220 that is connected to a distal end of the insertion section body 2000 with a shaft member 210.

In this embodiment, the insertion section 160 is formed of a material having constant rigidity and hardly bent, such as metal or resin having high biocompatibility.

The rotating member 220 includes a disk-like top plate portion 230 and a substantially cylindrical connection portion 240 connected to a proximal end surface of the top plate portion 230. The top plate portion 230 and the connection portion 240 are formed integrally. A through-hole 230a passing in the direction of the axis line C20 of the insertion section 160 is formed in the top plate portion 230.

Figure 52:
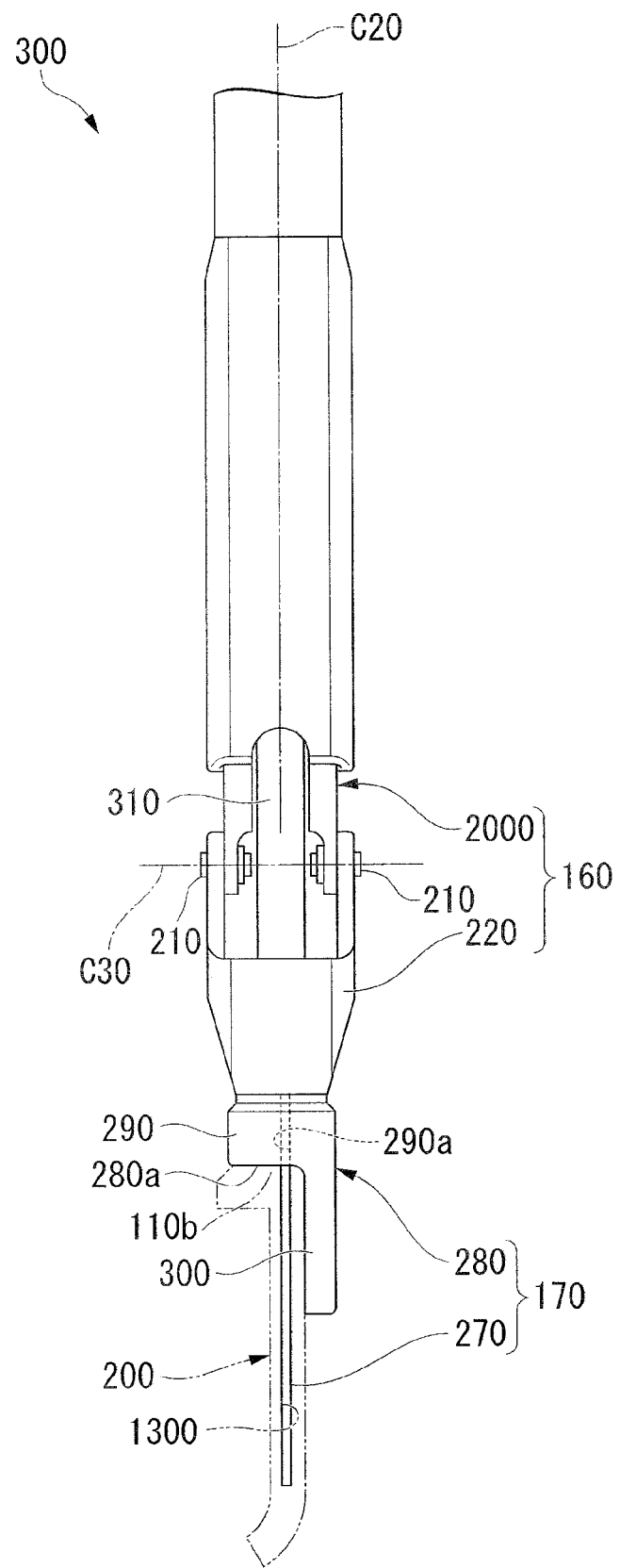
FIG. 52 is a side view illustrating the distal end of the treatment tool of the electrode implanting system.

As shown in FIG. 52, a pair of shaft members 210 is disposed in the axis line (predetermined axis line) C30 with a coil sheath 310 (to be described later) interposed therebetween. The rotating member 220 is connected to the insertion section body 2000 with the shaft members 210, whereby it can rotate about the axis line C30 of the shaft members 210.

As shown in FIGS. 50 and 52, the stretch mechanism 170 includes a switching rod (stretch member) 270 that has a rod shape and is inserted the insertion section body 2000 and a holder 280 that is connected to a distal end surface of the rotating member 220.

The holder 280 includes a base member 290 having a substantially cylindrical shape and a tongue-like member 300 extending forward from an edge of a distal end surface of the base member 290. The base member 290 and the tongue-like member 300 are integrally formed out of the same material as the insertion section body 2000. A stepped portion 280a is formed in the connecting portion between the base member 290 and the tongue-like member 300. A through-hole 290a that extends in the axis line direction of the base member 290 and is opened from the stepped portion 280a is formed in the base member 290.

The stepped portion 280a of the holder 280 is formed in a shape corresponding to an end portion 110b of the electrode support 110 at which the opening of the guide hole 1300 is formed. When the end portion 110b of the electrode support 110 comes in contact with the stepped portion 280a of the holder 280, the guide hole 1300 of the electrode unit 200 communicates with the through-hole 290a of the holder 280.

As shown in FIG. 50, the coil sheath 310 is disposed in the insertion section body 2000, and a distal end of the coil sheath 310 is attached to the inner circumferential surface of the through-hole 230a of the rotating member 220.

A distal end of the switching rod 270 extends forward from the holder 280 through the through-hole 290a of the holder 280. On the other hand, a proximal end of the switching rod 270 is connected to the operation unit 190 along with the coil sheath 310 through the inside of the coil sheath 310. The switching rod 270 is disposed to move forward and backward inside the holder 280 and the coil sheath 310. The switching rod 270 is set so that the distal end thereof detachably engages with the guide hole 1300 of the electrode support 110.

According to the switching rod 270 having the above-mentioned configuration, the switching rod 270 is inserted into the guide hole 1300 by pushing the switching rod 270 into the insertion section 160 in the state where the end portion 110b of the electrode unit 200 contacts and engages with the stepped portion 280a of the holder 280. Accordingly, the switching rod 270 switches the shape of the electrode unit 200 from the curved shape to the stretched shape and holds the switched shape. By towing the switching rod 270, it is possible to remove the switching rod 270 from the guide hole 1300 of the electrode unit 200 and to release the holding of the electrode unit 200.

As shown in FIG. 50, the adjusting mechanism 180 includes an operation member 340 of which a distal end is connected to the rotating member 220 and a proximal end is connected to the operation unit 190. The operation member 340 includes a rod 350 of which a distal end is connected to the rotating member 220 so as to rotate around the axis line C40 and an operation wire 360 of which a distal end is connected to a proximal end of the rod 350 and which is inserted through the insertion section body 2000. As shown in FIG. 51, a protrusion 370 protruding substantially in parallel to the axis line C40 is formed at the proximal end of the rod 350.

A guide hole 200a extending in the direction of the axis line C20 is formed in the insertion section body 2000. The protrusion 370 of the rod 350 engages with the guide hole 200a so as to move in the guide hole 200a in the direction of the axis line C20.

As shown in FIG. 50, in the adjusting mechanism 180 having the above-mentioned configuration, when the operation wire 360 is towed relative to the insertion section 160, the rotating member 220 rotates around the axis line C30. Since the rod 350 is connected to the rotating member 220 so as to rotate around the axis line C40, the rod 350 moves to the position A and the operation member 340 is curved. In this embodiment, the switching rod 270 is located outside the curved portion B formed by the operation member 340 when the operation wire 360 is towed.

Figure 53:
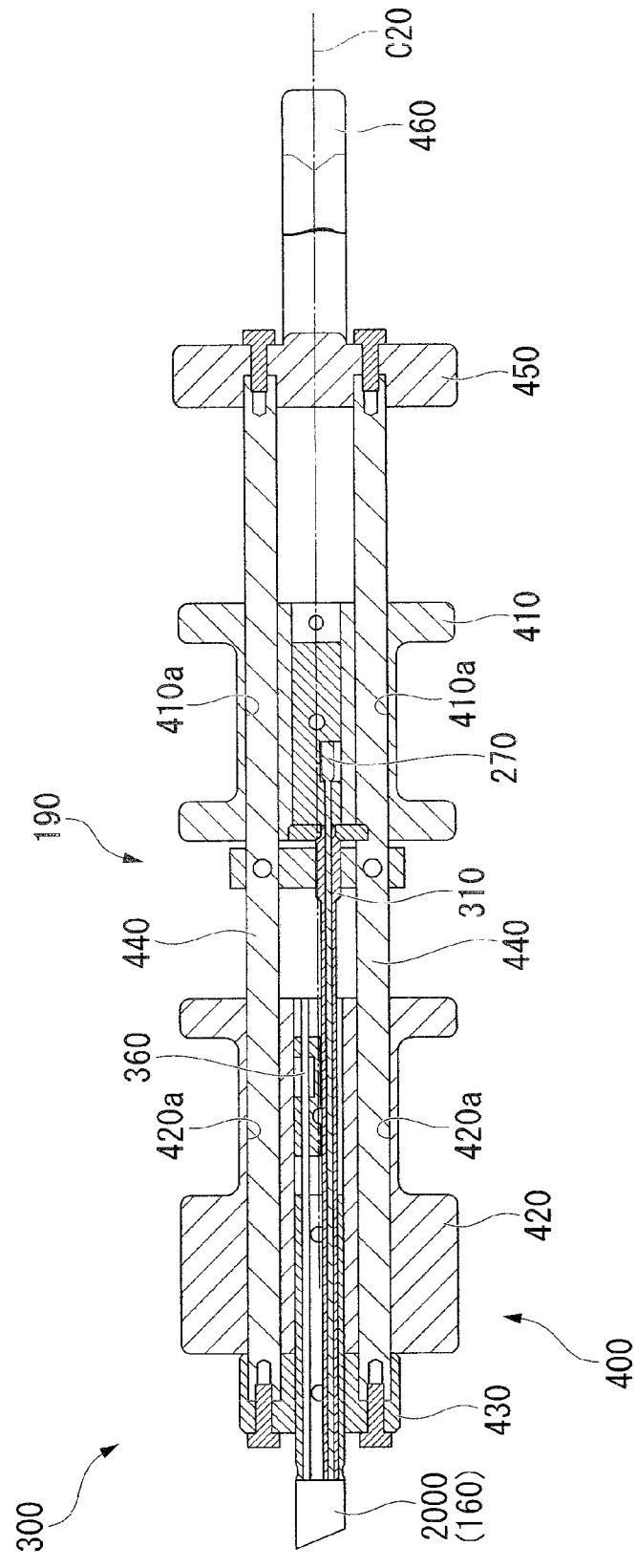
FIG. 53 is a front sectional view illustrating a proximal end of the treatment tool of the electrode implanting system.

As shown in FIG. 53, the operation unit 190 includes an operation unit body 400 connected to a proximal end of the insertion section body 2000 and a stretch lever 410 and an adjusting lever 420 connected to the operation unit body 400 so as to slide in the direction of the axis line C20.

The operation unit body 400 includes a distal end fixing member 430 fixed to the outer circumferential surface of the proximal end of the insertion section body 2000, a pair of guide rods 440 of which distal ends are attached to the distal end fixing member 430 and which extend in the direction of the axis line C20 with a constant distance therebetween in parallel, and a proximal end fixing member 450 that fixes proximal ends of the pair of guide rods 440.

The stretch lever 410 has a substantially cylindrical shape. An insertion hole 410a through which the pair of guide rods 440 is inserted in the axis line direction is formed in the stretch lever 410. The proximal end of the switching rod 270 is fixed to the stretch handle 410, and thus the switching rod 270 can be towed from or pushed into the coil sheath 310 by causing the stretch lever 410 to slide relative to the pair guide rods 440.

The adjusting lever 420 has a substantially cylindrical shape similarly to the stretch lever 410, and an insertion hole 420a through which the pair of guide rods 440 is inserted is formed. The adjusting lever 420 is disposed closer to the distal end than the stretch lever 410. A proximal end of the operation wire 360 is fixed to the adjusting lever 420, and thus the operation wire 360 can be towed from or pushed into the insertion section 160 by causing the adjusting lever 420 to slide.

A finger rest 460 on which an operator rests a finger is disposed at the proximal end of the proximal end fixing member 450.

Figure 54:
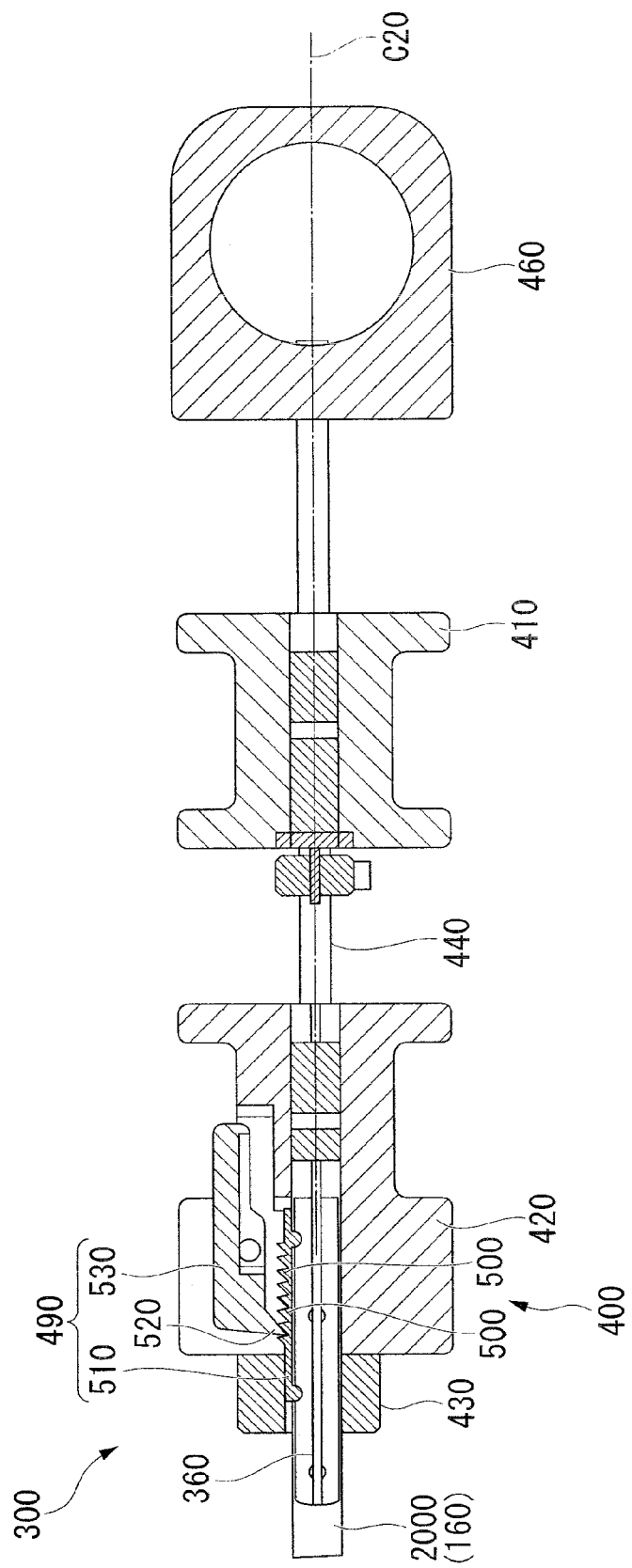
FIG. 54 is a side sectional view illustrating the proximal end of the treatment tool of the electrode implanting system.
Figure 55:
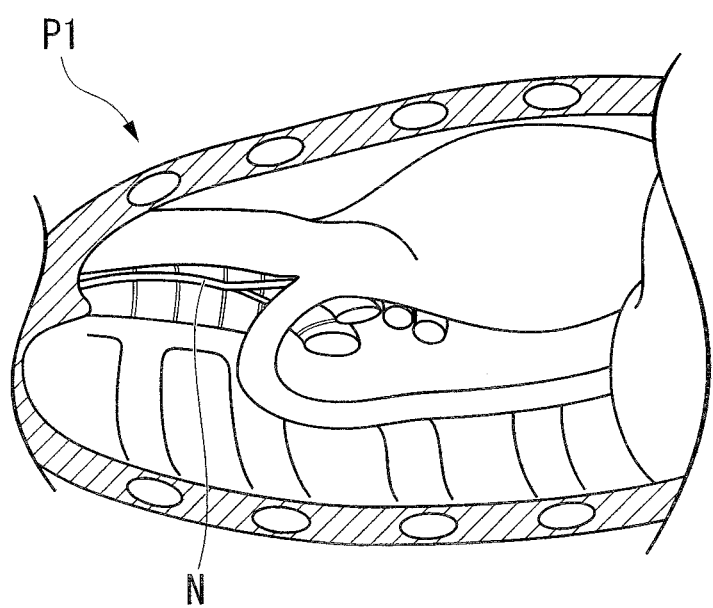
FIG. 55 is a diagram illustrating a position of a nerve tissue in a patient's chest cavity.

As shown in FIG. 54, the treatment tool 300 according to this embodiment includes a fixing mechanism 490 that fixes the position of the proximal end of the operation wire 360 to the insertion section 160 and releases the fixation.

The fixing mechanism 490 includes a base member 510 that is fixed to the outer circumferential surface of the proximal end of the insertion section body 2000 and in which plural locked portions 500 are formed on the outer circumferential surface in parallel in the direction of the axis line C20 and a switching lever 530 that is rotatably supported by the adjusting lever 420 and in which a locking portion 520 formed at the distal end is locked to the locked portions 500. An urging spring not shown is disposed in the switching lever 530. The urging spring urges the locking portion 520 of the switching lever 530 to the locked portions 500. When the locking portion 520 is locked between the locked portions 500, the adjusting lever 420 is fixed to the insertion section 160 in the direction of the axis line C20. On the other hand, when the locking portion 520 is separated from the locked portions 500, the fixation is released.

In this embodiment, when the position at which the locking portion 520 is locked to the locked portions 500 moves in the direction of the axis line C20 by a width of a single locked portion 500, the angle of the rotating member 220 about the axis line C30 relative to the insertion section body 2000 varies, for example, by 10°.

The thoracoscope 600 emits illumination light forwardly from a distal end of the observation insertion section 500 and observes the reflected light from a front side by the use of an observation unit (not shown) disposed at the distal end of the observation insertion section 500.

The nerve stimulator 700 includes a power source not shown, detects an electrical signal generated from a nerve tissue, and generates an electrical stimulus with a predetermined waveform. Accordingly, the nerve stimulator 700 detects a signal of the nerve tissue acquired by the electrode unit 200 and applies the electrical stimulus to the nerve tissue as needed.

The lead body 800 has a known configuration and includes a coil (not shown) electrically connecting the electrode 120 to the nerve stimulator 700 and a flexible insulating tube 540 (see FIG. 47) covering the outer circumference of the coil.

A process of implanting the electrode unit into a nerve tissue (linear tissue) N in a chest cavity of a patient P1, which is carried out by the use of the electrode implanting system 100 having the above-mentioned configuration, will be described with reference to FIGS. 55 to 62. An example of the nerve tissue to which the process is applied is a nerve tissue in a superior vena cava.

This process includes four steps of an opening forming step of forming an opening in a patient's body wall, an attachment and introduction step of attaching the electrode unit 200 to the treatment tool 300 and introducing the electrode unit 200 into the inside through the opening, a position adjusting step of adjusting the orientation of the electrode unit 200 relative to the never tissue N, and a leaving step of winding the electrode unit 200 around the nerve tissue N and leaving the electrode unit.

Figure 56:
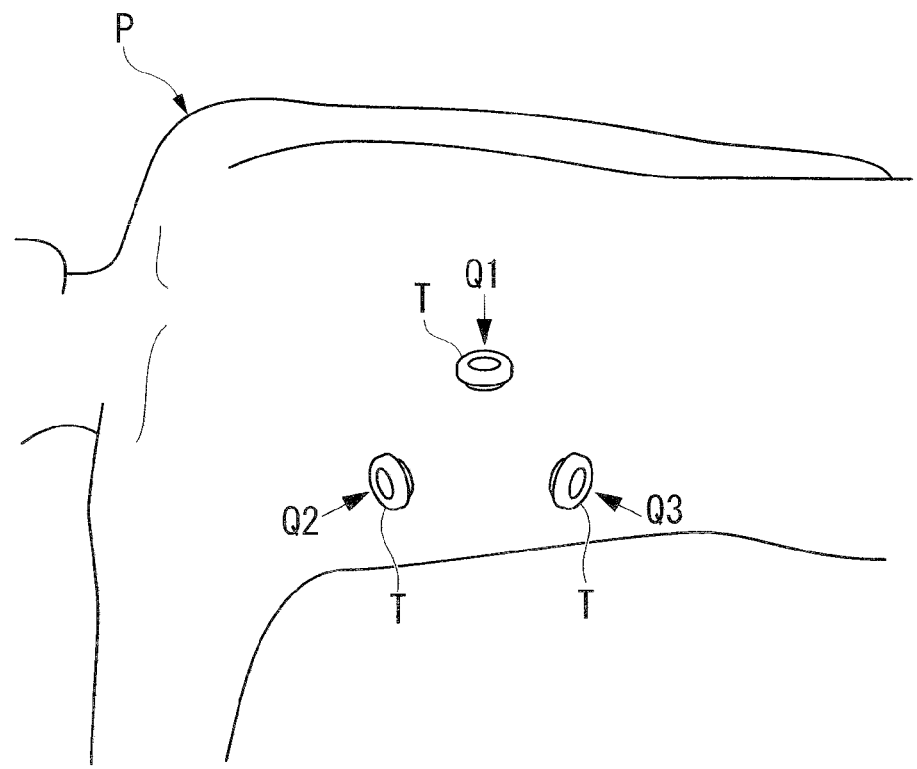
FIG. 56 is a diagram illustrating a state where trocars are inserted into openings formed in a patient's chest region.

First, an operator forms three openings not shown in the chest of the patient P1 by the use of a knife or the like and inserts trocars T into the openings (opening forming step), as shown in FIG. 56.

Figure 57:
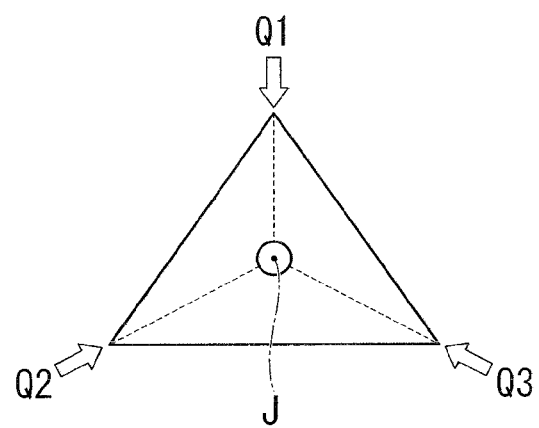
FIG. 57 is a diagram illustrating the positional relationship among the openings.

As shown in FIG. 57, the positions Q1 to Q3 of the openings are preferably located substantially at equal angular intervals around a reference axis J as viewed in the direction of the reference axis J extending perpendicular to the paper surface. By locating the positions Q1 to Q3 in this way, it is easy to perform the treatment using the treatment tool 300 or the like while observing the inside of the chest cavity using the thoracoscope 600 in the subsequent steps.

The electrode unit 200 is attached to the treatment tool 300 and the electrode unit 200 is introduced into the chest cavity through the trocar T (attachment and introduction step).

The observation insertion section 500 of the thoracoscope 600 is introduced through the trocar T located at the position Q1 to observe the inside of the chest cavity, a peeling forceps not shown is introduced through the trocar T located at the position Q2, and a membrane around the nerve tissue N is incised to expose the nerve tissue N. Then, the peeling forceps is pulled out through the trocar T.

Figure 58:
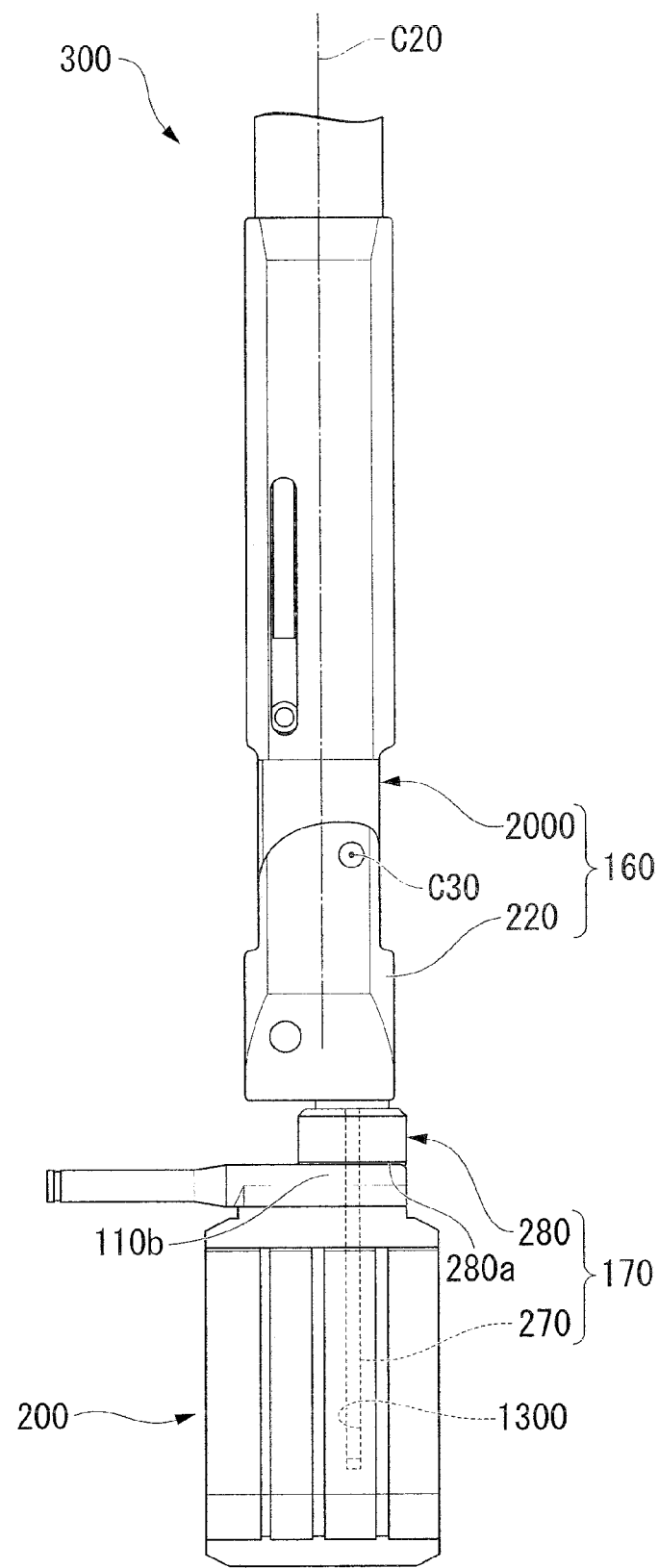
FIG. 58 is a diagram illustrating a state where the electrode unit is attached to a holder of the treatment tool of the electrode implanting system.

Outside the body, as shown in FIG. 58, when the stretch lever 410 is moved to the distal end relative to the operation unit body 400 in the state where the end portion 110b of the electrode unit 200 engages with the stepped portion 280a of the holder 280, the switching rod 270 is pushed out from the holder 280 to the distal end and the switching rod 270 is inserted into the guide hole 1300 of the electrode unit 200. Accordingly, the shape of the electrode unit 200 is stretched along the shape of the switching rod 270 and is switched from the curved shape to the stretched shape, whereby the electrode unit 200 is attached to the holder 280.

Subsequently, the insertion section 160 of the treatment tool 300 to which the electrode unit 200 having the stretched shape is attached is introduced into the chest cavity through the trocar T located at the position Q2.

The orientation of the electrode unit 200 relative to the nerve tissue N is adjusted (position adjusting step).

Figure 59:
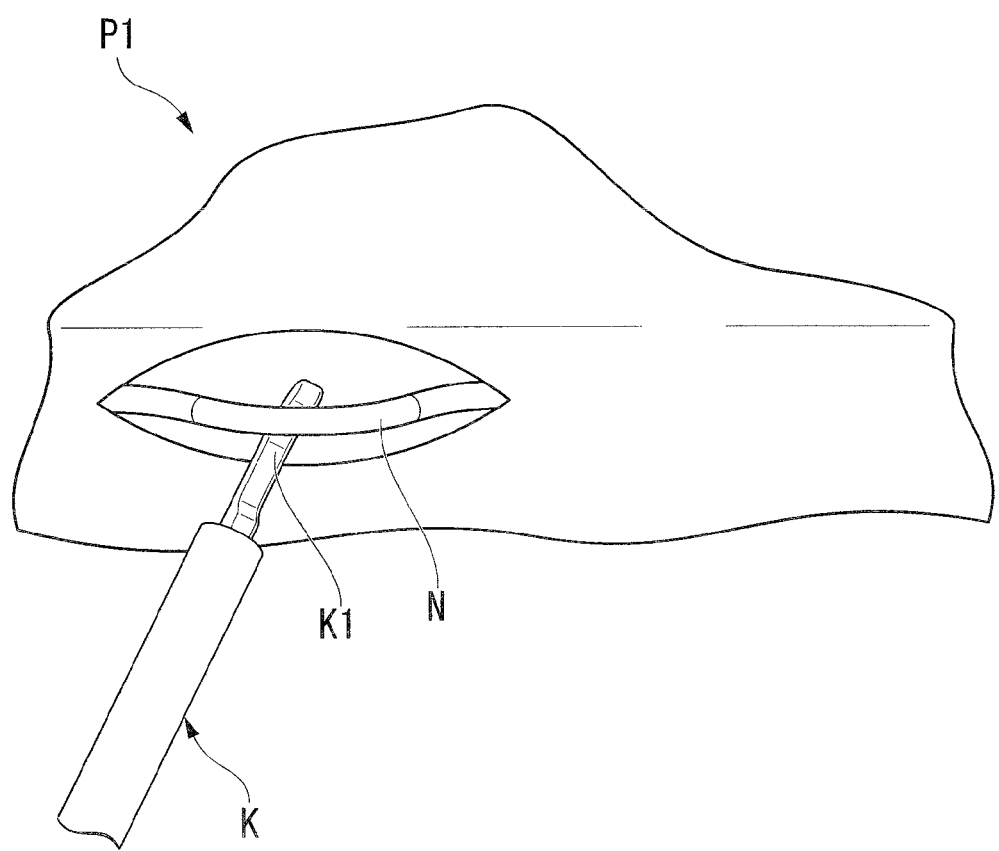
FIG. 59 is a diagram illustrating a state where a nerve tissue is lifted from peripheral tissues with a forceps.

First, as shown in FIG. 59, a forceps K is introduced into the chest cavity through the trocar T located at the position Q2 and the nerve tissue N is lifted from the peripheral tissue by the use of a distal end K1 of the forceps K. This state is maintained.

Figure 60:
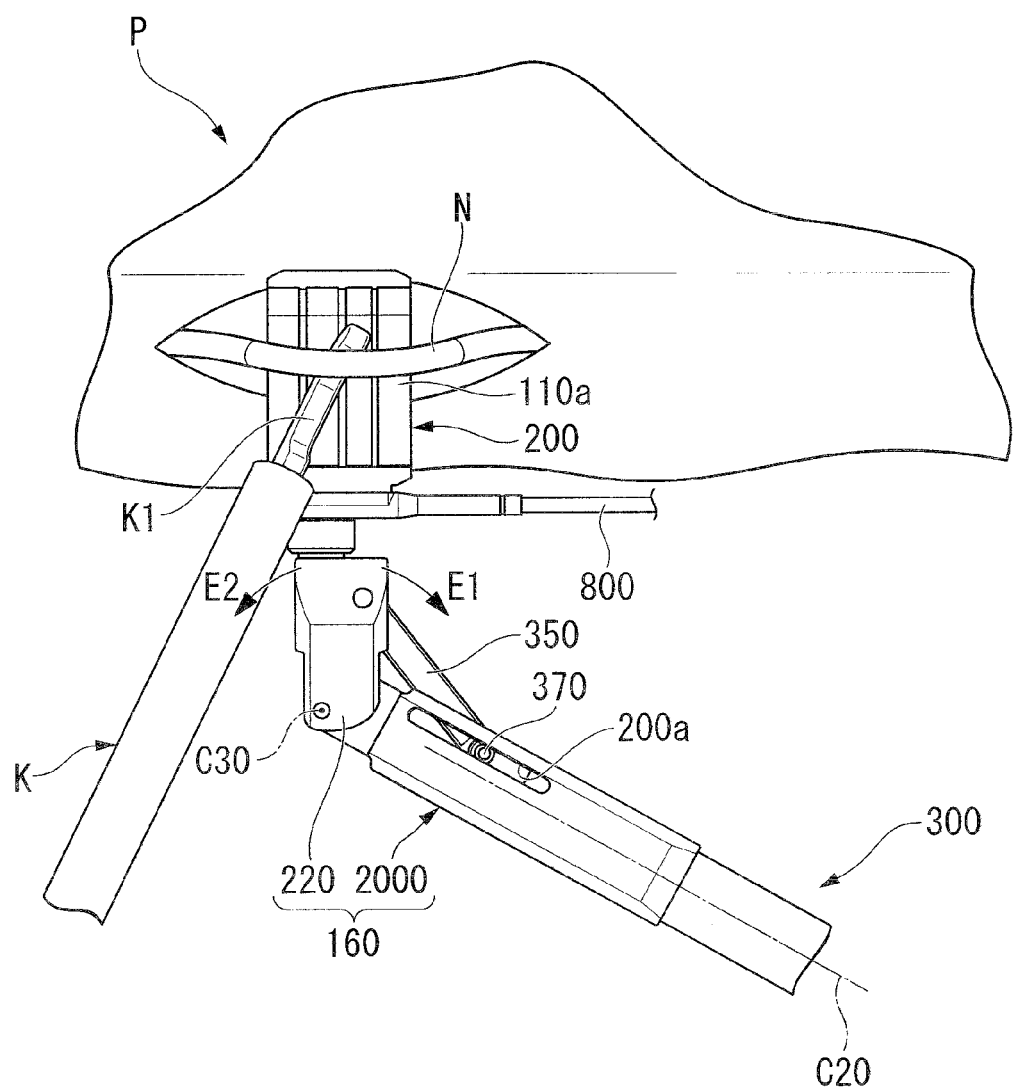
FIG. 60 is a diagram illustrating a state where the distal end of the insertion section of the treatment tool of the electrode implanting system is bent.

As shown in FIG. 60, the operator moves the treatment tool 300 to cause the electrode unit 200 to get close to the nerve tissue N. This step of lifting the nerve tissue N by the use of the forceps K to guarantee a gap for insertion of the electrode unit 200 is referred to as a lifting step. When the nerve tissue can be exposed, the electrode unit and the treatment tool may be inserted under the nerve tissue without using the forceps K.

Here, when the adjusting lever 420 is moved to the proximal end relative to the operation unit body 400, the operation wire 360 is towed relative to the insertion section 160. At this time, the rod 350 connected to the operation wire 360 also moves to the proximal end as shown in FIG. 60. The protrusion 370 formed at the proximal end of the rod 350 moves to the proximal end in the direction of the axis line C20 inside the guide hole 200a. Since the rotating member 220 can rotate around the axis line C30, a distal end of the rod 350 moves in the direction in which it is separated from the axis line C20 and the rotating member 220 is bent (rotated) in a bending direction E1.

When the adjusting lever 420 is moved to the distal end relative to the operation unit body 400, the operation wire 360 is pushed in and the rotating member 220 is bent in a bending direction E2 which is opposite to the bending direction E1.

In this way, by adjusting the orientation of the electrode unit 200 relative to the nerve tissue N or adjusting the orientation of the insertion section 160 by the use of the adjusting lever 420, the first surface 110a of the electrode unit 200 faces the nerve tissue N and the orientation of the electrode unit 200 is adjusted so that the nerve tissue N is substantially parallel to the direction of the axis line C10 of the curved shape of the electrode unit 200.

Subsequently, the electrode unit 200 is wound around the nerve tissue N and is left (leaving step).

Figure 61:
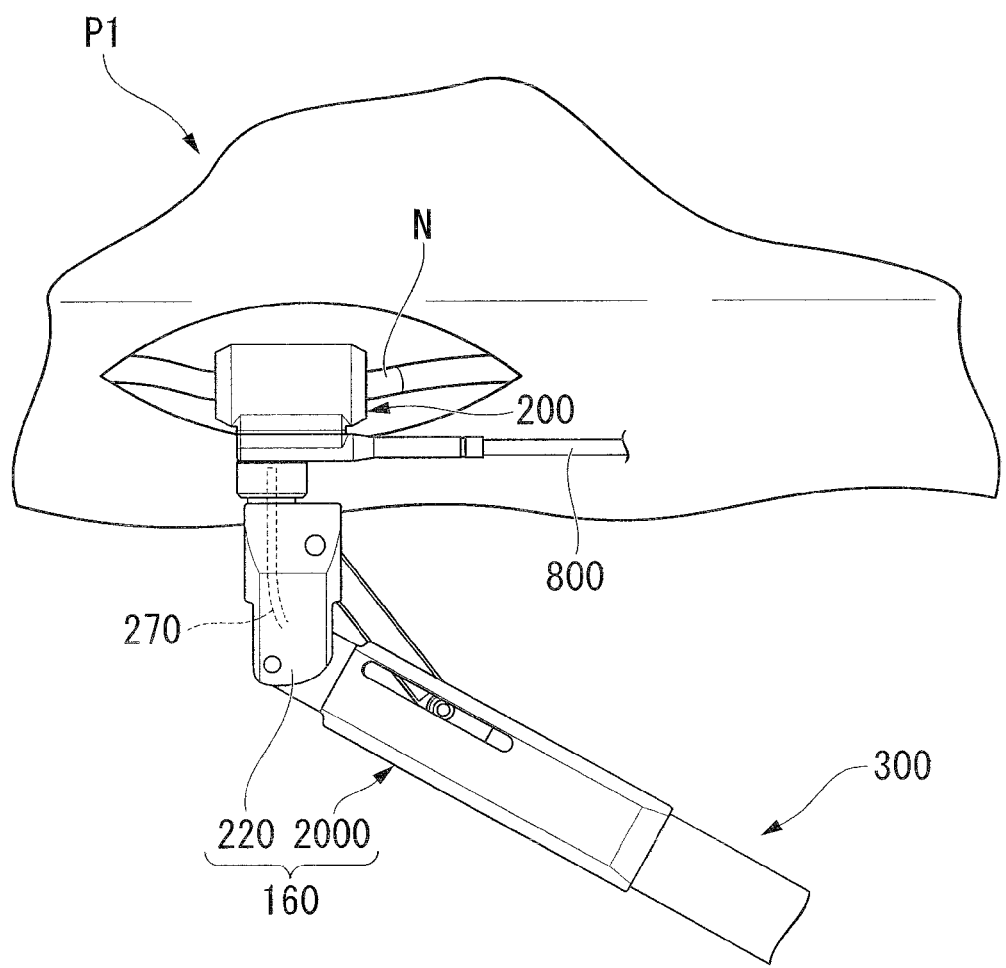
FIG. 61 is a diagram illustrating a state where the electrode unit of the electrode implanting system is wound around a nerve tissue.
Figure 62:
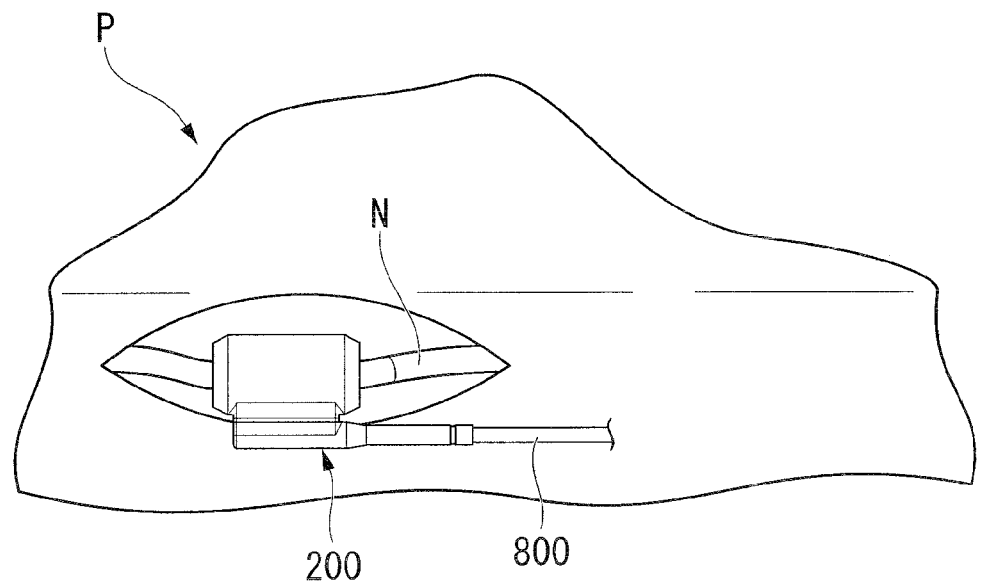
FIG. 62 is a diagram illustrating a state where the electrode unit is implanted in the chest cavity.

First, the distal end K1 of the forceps K is separated from the nerve tissue N. By moving the stretch lever 410 to the proximal end relative to the operation unit body 400, the switching rod 270 is removed from the guide hole 1300 of the electrode unit 200. Then, the electrode unit 200 having been stretched in the stretched shape by the switching rod 270 is returned to the curved shape in the natural state by means of the its elastic force and is wound around the nerve tissue N as shown in FIG. 61, and the electrode unit 2 is separated from the treatment tool 300.

Thereafter, the forceps K and the treatment tool 300 are pulled out from the trocars T, the membrane around the nerve tissue N is sutured, the trocars T are detached from the patient P1, and the openings formed in the chest are sutured. In this way, the step of pulling out the treatment tool 300 from the chest cavity is referred to as a pullout step.

The lead body 800 and the nerve stimulator 700 are buried under the skin of the patient P1 and the process is ended.

The above-mentioned process includes an arrangement step of arranging the thoracoscope 900, the nerve tissue N, the forceps K lifting the nerve tissue to guarantee the gap, the electrode unit 200, and the treatment tool 300 in this order. The arrangement step is effective for reducing the possibility that, for example, the arranged positions of the electrode unit 200 and the treatment tool 300 intercept the viewing field of the thoracoscope 600 so as not to observe the nerve tissue N. Therefore, by further providing the arrangement step of arranging the elements in the above-mentioned order, it is possible to satisfactorily guarantee the viewing field of the thoracoscope 600.

As described above, by using the electrode implanting system 1 according to this embodiment, the operator switches the electrode unit 200 having the curved shape in the natural state to the stretched shape by the use of the stretch mechanism 170, adjusts the orientation of the electrode unit 200 by the use of the adjusting mechanism 180, and arranges the electrode unit 200 so that the first surface 110a of the electrode unit 200 faces the nerve tissue N. By switching the shape of the electrode unit 200 to the curved shape by the use of the stretch mechanism 170, the electrode unit 200 is wound around the nerve tissue N while bringing the electrode 120 into contact with the nerve tissue N.

Accordingly, even when a nerve tissue N is surrounded with complex tissues, it is possible to satisfactorily and easily wind the electrode unit 200 around the nerve tissue N, by switching the electrode unit 200 to the stretched shape, adjusting the orientation of the electrode unit 200, and causing the electrode unit to get close to the nerve tissue N.

The guide hole 1300 extending in parallel to the curving direction D1 is fainted in the electrode support 110, and the stretch mechanism 170 includes the switching rod 270 of which the distal end detachably engages with the guide hole 1300 and the holder 280 connected to the distal end of the insertion section 160. Therefore, by inserting the switching rod 270 into the guide hole 1300 of the electrode unit 200 or removing the switching rod from the guide hole 1300, the shape of the electrode unit 200 can be easily switched between the curved shape and the stretched shape.

By bringing the holder 280 into contact with the electrode unit 200, the switching rod 270 can be easily removed from the guide hole 1300.

The adjusting mechanism 180 can bend the distal end of the insertion section 160 in the direction in which it is separated from the axis line C20 of the insertion section 160. Accordingly, it is possible to easily adjust the orientation of the electrode unit 200 attached to the distal end of the insertion section 160.

The insertion section 160 includes the insertion section body 2000 and the rotating member 220 connected to the distal end of the insertion section body 2000 so as to rotate around the axis line C30. The adjusting mechanism 180 includes the operation member 340 of which a distal end is connected to the rotating member 220. Therefore, by moving the operation member 340 forwardly and backwardly, it is possible to bend the distal end of the insertion section 160 around the axis line C30.

Since the treatment tool 30 includes the fixing mechanism 490 fixing the position of the proximal end of the operation member 340 relative to the insertion section 160 and releasing the fixation, it is possible to easily hold the shape of the distal end of the insertion section 160 bent by a predetermined amount.

When the distal end of the insertion section 160 is bent, the switching rod 270 is located in the outside of the curved portion B formed by the operation member 340. Accordingly, the radius of curvature of the switching rod 270 can be set to be greater than the radius of curvature of the curved portion B, thereby preventing the switching rod 270 from having difficulty moving forward and backward due to the contact with the peripheral elements of the coil sheath 310 or the like.

In this embodiment, since the electrode implanting system 100 includes the electrode implanting apparatus 400 and the thoracoscope 600, it is possible to wind the electrode unit 200 around the nerve tissue N by the use of the electrode implanting apparatus 400 while observing the inside of the chest cavity by the use of the observation insertion section 500 of the thoracoscope 600.

Hitherto, the embodiments of the invention have been described in detail with reference to the accompanying drawings, but the specific configurations are not limited to the embodiments and may be modified in various forms without departing from the concept of the invention.

Figure 63:
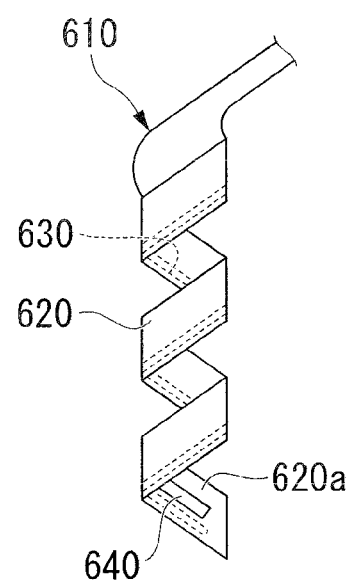
FIG. 63 is a diagram illustrating the entire configuration of an electrode unit according to a modified example of this embodiment.

For example, the electrode implanting system 1 according to the above-mentioned embodiment includes the electrode unit 200 curved around the axis line C10 in the natural state as the electrode unit. However, as shown in FIG. 63, an electrode unit 610 may be provided which is wound around a nerve tissue N in a helical shape about a predetermined direction in the natural state where an external force does not act thereon.

In the electrode unit 610, a helical guide hole 630 is formed in an electrode support 620 formed in a helical shape and an electrode 640 is formed on the inside surface 620a of the electrode support 620.

Figure 64:
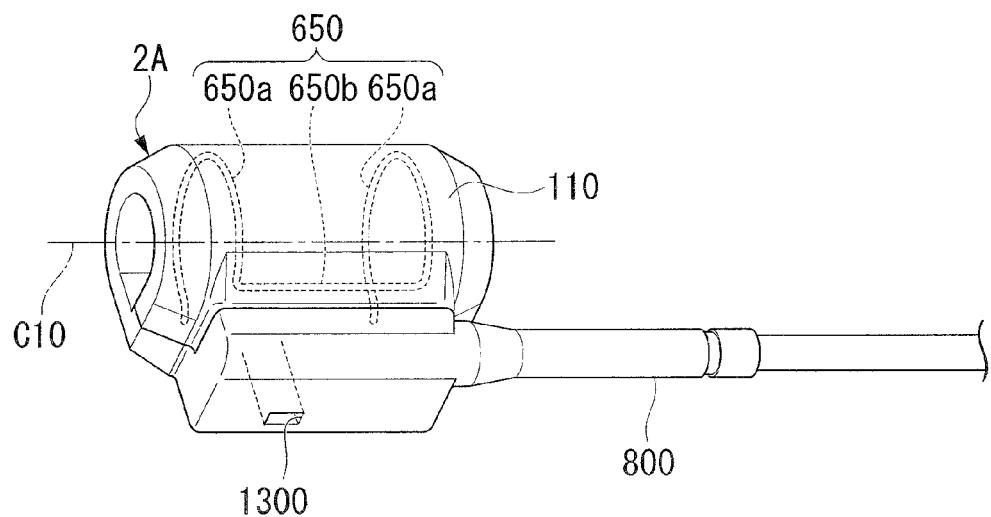
FIG. 64 is a perspective view illustrating the electrode unit according to another modified example of this embodiment.

An electrode unit 2A shown in FIG. 64 may be provided instead of the electrode unit 200 according to the above-mentioned embodiment. The electrode unit 2A includes a spring member 650 formed of, for example, a nickel-titanium hyperelastic wire and buried in the electrode support 110 in addition to the configurations of the electrode unit 200. The spring member 650 includes a pair of arms 650a curved around the axis line C10 and disposed with an interval in the direction of the axis line C10 and a connection portion 650b connecting the ends of the pair of arms 650a. The arms 650a have a curved shape in the natural state where an external force does not act thereon and are switched to a substantially straight line when the electrode unit 2A is changed to the stretched shape.

Since the electrode unit 2A includes the spring member 650, it is possible to improve the holding force for winding the electrode unit around a linear tissue such as a nerve tissue N. In this way, the holding force of the electrode unit may be properly adjusted depending on the characteristics or the like of the linear tissue as an implanting target.

In the electrode implanting system 100 according to the above-mentioned embodiment, the holder 280 may be connected to the rotating member 220 so as to rotate around the axis line of the through-hole 230a of the rotating member 220 and the stretch lever 410 may be allowed to rotate around the center axis line of the switching rod 270.

Accordingly, the stretch mechanism 170 including the switching rod 270 and the holder 280 can rotate around the center axis line of the switching rod 270. Therefore, by causing the stretch lever 410 to rotate around the center axis line of the switching rod 270, the electrode unit 200 attached to the holder 280 can be allowed to rotate around the center axis line of the switching rod 270, thereby adjusting the orientation of the electrode unit 200.

Figure 65:
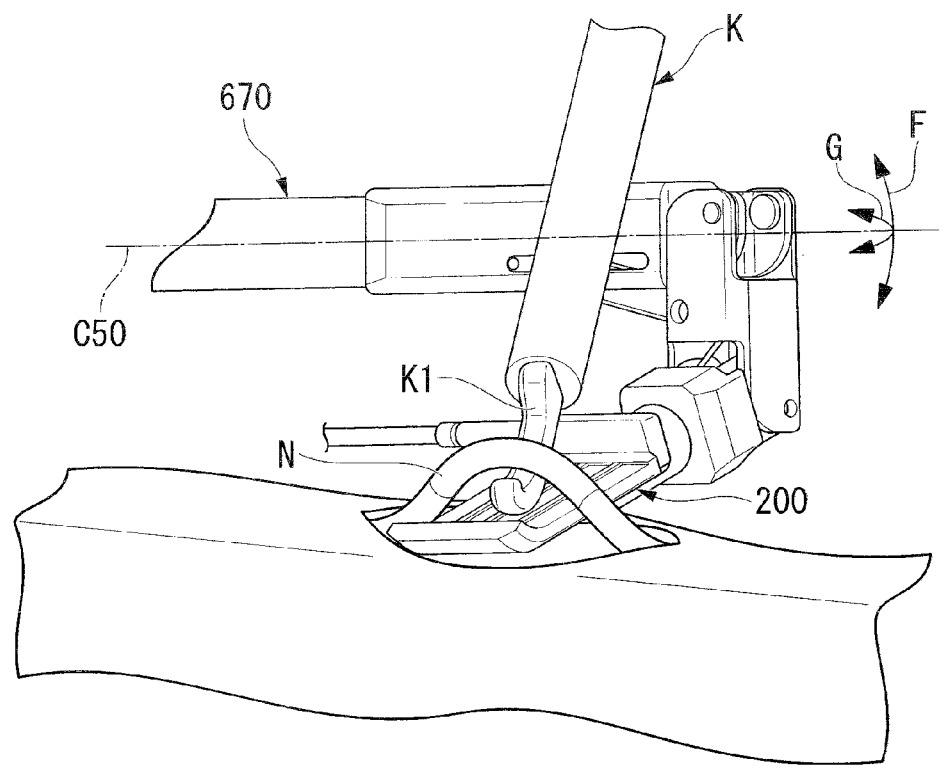
FIG. 65 is a diagram illustrating the distal end of a treatment tool according to another modified example of this embodiment.

In the above-mentioned embodiment, as shown in FIG. 65, an adjusting mechanism not shown may be constructed so as to bend the distal end of the insertion section 670 in a first direction F and a second direction G which are separated from the direction of the axis line C50 of the insertion section 670 and intersected by each other. Accordingly, it is possible to bend the distal end of the insertion section 670 with a higher degree of freedom.

In the above-mentioned embodiment, when a nerve tissue N is located at a directly-visible position, the thoracoscope 600 may not be used. When the viewing field of the thoracoscope 600 can be enlarged for observation, it is possible to implant a smaller electrode unit into a small linear tissue.

In the above-mentioned embodiment, as viewed in the direction of the axis line C30 defined by the shaft member 210, the operation member 340 may be disposed on both sides with the axis line C30 interposed therebetween and the distal ends of the operation members 340 may be connected to the rotating member 220.

In general, when an operation wire is used as the operation member 340, it is more easier in operation to tow the operation wire. Accordingly, even when the operation wire is used as the operation member 340, it is possible to satisfactorily operate the rotating member 220 in the bending direction E1 and the bending direction E2 shown in FIG. 60.

Although it has been described that the electrode implanting system according to this embodiment is used in the medical field, the electrode implanting system is not limited to the medical field, but may be used in the industrial fields. For example, when a cable (linear tissue) in which predetermined current flows is disposed inside a space communicating with a narrow opening, an electrode implanting system including an electrode unit as a probe for measuring the current flowing in the cable and a treatment tool used to wind the electrode unit around the cable through the opening can be used for industrial purposes.

In this case, an electrode in the electrode unit may be buried in an electrode support without exposing the electrode from one surface of the electrode support.

By employing the electrode unit and the electrode system according to the invention, it is possible to satisfactorily and easily attach the electrode unit to a linear tissue of a biological body.

By employing the electrode implanting apparatus and the electrode implanting system according to the invention, it is possible to wind the electrode unit around a linear tissue while adjusting the orientation of the electrode unit.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. An electrode system comprising:
an electrode unit capable of switching at least a part of its shape between a curved shape and a stretched shape, wherein in the curved shape the electrode unit is wound around a predetermined linear tissue, and wherein in the stretched shape the electrode unit is flat; and
a treatment tool that switches the shape of the at least a part of the electrode unit between the curved shape and the stretched shape,
wherein the electrode unit includes:
an insulating member formed in a sheet shape out of an elastic material; and
an electrode that is disposed on a first surface which is an inside surface of a curvature when the insulating member has a curved shape and which applies a predetermined voltage,
wherein the insulating member has the curved shape when an external force is not applied,
wherein the treatment tool comprises a stretch mechanism that switches the curved shape of the electrode unit to the stretched shape, holds the stretched shape, and releases the holding, wherein the stretch mechanism comprises a stretch member formed of a material having a higher rigidity than that of the insulating member, and wherein the stretch member is capable of sliding relative to the insulating member to cause the insulating member to form the curved shape or the stretched shape.

2. The electrode system according to claim 1, wherein the insulating member includes an electrode-side engagement portion extending in parallel to the curving direction of the insulating member, and wherein the stretch mechanism includes:

the stretch member that is formed to extend in a predetermined direction out of a material having higher rigidity than that of the insulating member and detachably engages with the electrode-side engagement portion of the insulating member; and a contact member that comes in contact with the insulating member when the stretch member is disengaged from the insulating member.

3. The electrode system according to claim 2, wherein the electrode-side engagement portion is formed at both ends in an axis line direction of the curvature when the insulating member has a curved shape, and wherein the stretch mechanism further includes:

two stretch members; and a member gap adjusting section that supports the two stretch members to be arranged in a direction intersecting the predetermined direction in which each of the two stretch members extends and adjusts the gap between the two stretch members in the intersecting direction.

4. The electrode system according to claim 1, wherein the stretch mechanism pinches the electrode unit from the first surface of the insulating member and a second surface opposite to the first surface so as to hold the electrode unit in the stretched shape, and releases the pinching.

5. The electrode system according to claim 4, wherein the stretch mechanism includes:

a tubular member that receives the electrode unit extending in a predetermined electrode-unit stretching direction by stretching the curvature of the electrode unit having the curved shape so as to allow the electrode-unit stretching direction to be parallel to the axis line direction of the tubular member; and an extrusion member that extrudes the electrode unit in the tubular member to the distal end of the tubular member in the axis line direction.

6. The electrode system according to claim 4, wherein in a state where the curvature of the electrode unit having the curved shape is stretched to extend in a predetermined electrode-unit stretching direction, the stretch mechanism includes:

a first pinch member that is disposed on the first surface of the insulating member and is movable to one side in the electrode-unit stretching direction;

a second pinch member that is disposed on the second surface of the insulating member; and a support member that comes in contact with one side of the insulating member in the electrode-unit stretching direction.

7. The electrode system according to claim 1, wherein the stretch mechanism includes:

a first end holding portion that holds a first end in the curving direction of the insulating member in the at least a part of the insulating member;

a second end engaging portion that engages with a second end in the curving direction of the insulating member in the at least a part of the insulating member; and a gap adjusting mechanism that adjusts the gap between the first end holding portion and the second end engaging portion.

8. The electrode system according to claim 1, wherein the electrode unit has the stretched shape in a natural state when an external force does not act thereon, and wherein the treatment tool includes a curving mechanism that switches the shape of the electrode unit from the stretched shape to the curved shape.

9. The electrode system according to claim 8, wherein the insulating member includes an electrode-side engagement portion extending in parallel to the first surface, wherein the electrode unit includes a curving member that is formed in a curved shape so as to be wound around a predetermined linear tissue out of an elastic material having higher rigidity than that of the insulating member and that engages with the electrode-side engagement portion, and wherein the curving mechanism includes:

a grasp portion that grasps the insulating member;

a reinforcing member that is formed to extend in a predetermined direction with constant rigidity and that detachably engages with the electrode-side engagement portion of the insulating member; and an extrusion portion that holds the curving member in a state where the curving member is stretched in the curved-portion stretching direction in which the curvature of the curving member is stretched and that extrudes the curving member, which has been stretched in the curved-portion stretching direction, in the curved-portion stretching direction.

10. An electrode unit which has a curved shape in which at least a part of its shape is curved to be wound around a predetermined linear tissue in a natural state where an external force does not act thereon and which can switch the curved shape to a stretched shape in which the at least a part of its shape is flat, comprising:

an insulating member that is formed in a sheet shape out of an elastic material;

an electrode that is disposed on the inside surface of a curvature formed by a curved shape of the insulating member and which applies a predetermined voltage; and a treatment tool comprising a stretch mechanism that switches the curved shape of the electrode unit to the stretched shape, holds the stretched shape, and releases the holding, wherein the insulating member includes an electrode-side engagement portion that extends in parallel to a curving direction in which the insulating member is curved, wherein the stretch mechanism comprises a stretch member formed of a material having a higher rigidity than that of the insulating member, and wherein the stretch member is capable of sliding relative to the insulating member to cause the insulating member to form the curved shape or the stretched shape.

11. An electrode unit which has a stretched shape in which at least a part of its shape is stretched in a natural state when an external force does not act thereon and which can switch the stretched shape to a curved shape in which the at least a part of its shape is curved to be wound around a predetermined linear tissue, comprising:

an insulating member that is formed in a sheet shape out of an elastic material;

an electrode that is disposed on a first surface of the insulating member which is the inside surface of a curvature when the insulating member has a curved shape and which applies a predetermined voltage;

a curving member that is formed in a curved shape out of an elastic material having higher rigidity than that of the insulating member; and a treatment tool comprising a stretch mechanism that switches the curved shape of the electrode unit to the stretched shape, holds the stretched shape, and releases the holding, wherein the insulating member includes an electrode-side engagement portion that extends in parallel to the first surface of the insulating member and that engages with the curving member, wherein the stretch mechanism comprises a stretch member formed of a material having a higher rigidity than that of the insulating member, and wherein the stretch member is capable of sliding relative to the insulating member to cause the insulating member to form the curved shape or the stretched shape.

12. An electrode implanting apparatus comprising:
the electrode system according to claim 1 in which the treatment tool includes a long insertion section and the stretch mechanism is disposed at a distal end of the insertion section;
an adjusting mechanism that adjusts the orientation of the electrode unit held by the stretch mechanism; and
an operation unit that is disposed in a proximal end of the insertion section and that operates the stretch mechanism and the adjusting mechanism.

13. The electrode implanting apparatus according to claim 12, wherein the insulating member includes an electrode-side engagement portion that extends in parallel to the curving direction in which the insulating member is curved, and
wherein the stretch mechanism includes:
a stretch member of which a distal end detachably engages with the electrode-side engagement portion of the insulating member and a proximal end is connected to the operation unit; and
a holder that is connected to the distal end of the insertion section and that comes in contact with the electrode unit.

14. The electrode implanting apparatus according to claim 12, wherein the adjusting mechanism curves the distal end of the insertion section in a direction which is separated from an axis line of the insertion section.

15. The electrode implanting apparatus according to claim 14, wherein the insertion section includes:
a long insertion section body; and
a rotating member that is connected to the distal end of the insertion section body so as to rotate about a predetermined axis line and of which a distal end is connected to the holder, and
wherein the adjusting mechanism includes an operation member of which a distal end is connected to the rotating member and a proximal end is connected to the operation unit.

16. The electrode implanting apparatus according to claim 15, wherein the treatment tool includes a fixing mechanism that locks and unlocks the position of the proximal end of the operation member to and from the insertion section.

17. The electrode implanting apparatus according to claim 15, wherein the stretch member is disposed so as to be located outside the curvature of the operation member when the distal end of the insertion section is curved.

18. The electrode implanting apparatus according to claim 12, wherein the adjusting mechanism curves the distal end of the insertion section in a first direction and a second direction which depart from the axis line of the insertion section and intersect each other.

19. The electrode implanting apparatus according to claim 12, wherein the stretch mechanism rotates about the axis line of the stretch member.

20. An electrode implanting system comprising:
the electrode implanting apparatus according to claim 12; and
an observation device that includes a long observation insertion section.

21. The electrode system according to claim 1, wherein the electrode unit has the curved shape in which the at least a part of the electrode unit is curved to be wound around a predetermined linear tissue in a natural state when an external force does not act thereon and switches the shape to the stretched shape in which the at least a part of the electrode unit is flat, and
wherein the insulating member includes an electrode-side engagement portion that extends in parallel to the curving direction in which the insulating member is curved.

22. The electrode system according to claim 1, wherein the electrode unit has the stretched shape in which the at least a part of the electrode unit is stretched in a natural state when an external force does not act thereon and switches the shape to the curved shape in which the at least a part of the electrode unit is curved to be wound around a predetermined linear tissue,
wherein the electrode unit further includes a curving member that is formed in a curved shape out of an elastic material having higher rigidity than that of the insulating member, and
wherein the insulating member includes an electrode-side engagement portion that extends in parallel to the first surface of the insulating member and that engages with the curving member.

* * * * *